US006974830B2

(12) United States Patent
Bauer et al.

(10) Patent No.: US 6,974,830 B2
(45) Date of Patent: Dec. 13, 2005

(54) NR1H4 NUCLEAR RECEPTOR BINDING COMPOUNDS

(75) Inventors: Ulrike Bauer, Sandhausen (DE); Zach Cheruvallath, San Diego, CA (US); Ulrich Deuschle, Bammental (DE); Elena Dneprovskaia, San Diego, CA (US); Tim Gahman, Encinitas, CA (US); Kristina Giegrich, Lampertheim (DE); Ronnie Hanecak, San Clemente, CA (US); Normand Hébert, Cardiff, CA (US); John Kiely, San Diego, CA (US); Ingo Kober, Gaiberg (DE); Manfred Kögl, Eppelheim (DE); Harald Kranz, Leimen (DE); Claus Kremoser, Heidelberg (DE); Matthew Lee, Solana Beach, CA (US); Kerstin Otte, Heidelberg (DE); Carlton Sage, Cardiff, CA (US); Manish Sud, San Diego, CA (US)

(73) Assignee: Phenix Pharmaceuticals AG (DE)

( * ) Notice: Subject to any disclaimer, the term of this patent is extended or adjusted under 35 U.S.C. 154(b) by 0 days.

(21) Appl. No.: 10/185,731

(22) Filed: Jul. 1, 2002

(65) Prior Publication Data

US 2003/0149087 A1 Aug. 7, 2003

(30) Foreign Application Priority Data

Aug. 13, 2001 (EP) ............................................. 01119473

(51) Int. Cl.$^7$ ..................... A61K 31/426; C07D 277/20

(52) U.S. Cl. ..................... 514/370; 548/190; 548/193; 548/194

(58) Field of Search .................................. 548/190, 193, 548/194; 514/370

(56) References Cited

U.S. PATENT DOCUMENTS

| | | | |
|---|---|---|---|
| 2,863,874 A | * | 12/1958 | Gregory ..................... 548/190 |
| 5,464,847 A | | 11/1995 | Courtemanche et al. |
| 5,602,132 A | | 2/1997 | Roger et al. |
| 5,668,161 A | * | 9/1997 | Talley et al. ................. 514/365 |
| 5,856,347 A | | 1/1999 | Hashiguchi et al. |
| 6,051,574 A | | 4/2000 | Anthony |

FOREIGN PATENT DOCUMENTS

JP       09-235278       9/1997

OTHER PUBLICATIONS

Gregory et al (1958): STN International CAPLUS database, Columbus (Ohio),Accession No., 1959:51205.*

* cited by examiner

*Primary Examiner*—Golam M M Shameem
(74) *Attorney, Agent, or Firm*—Saliwanchik, Lloyd & Saliwanchik

(57) ABSTRACT

The present invention relates to compounds according to the general formula (I) which bind to the NR1H4 receptor and act as agonists of the NR1H4 receptor. The invention further relates to the treatment of diseases and/or conditions through binding of the nuclear receptor by the compounds and the production of medicaments using the compounds.

19 Claims, 14 Drawing Sheets

MGSKMNLIEH SHLPTTDEFS FSENLFGVLT EQVAGPLGQN LEVEPYSQYS NVQFPQVQPQ 60
ISSSSYYSNL GFYPQQPEEW YSPGIYELRR MPAETLYQGE TEVAEMPVTK KPRMGASAGR 120
IKGDELCVVC GDRASGYHYN ALTCEGCKGF FRRSITKNAV YKCKNGGNCV MDMYMRRKCQ 180
ECRLRKCKEM GMLAECMYTG LLTEIQCKSK RLRKNVKQHA DQTVNEDSEG RDLRQVTSTT 240
KSCREKTELT PDQQTLLHFI MDSYNKQRMP QEITNKILKE EFSAEENFLI LTEMATNHVQ 300
VLVEFTKKLP GFQTLDHEDQ IALLKGSAVE AMFLRSAEIF NKKLPSGHSD LLEERIRNSG 360
ISDEYITPMF SFYKSIGELK MTQEEYALLT AIVILSPDRQ YIKDREAVEK LQEPLLDVLQ 420
KLCKIHQPEN PQHFACLLGR LTELRTFNHH HAEMLMSWRV NDHKFTPLLC EIWDVQ 476

FIG. 4A
SEQ. ID NO. 1

```
atgggatcaa aaatgaatct cattgaacat tcccatttac ctaccacaga tgaatttct      60
ttttctgaaa atttatttgg tgttttaaca gaacaagtgg caggtcctct gggacagaac    120
ctggaagtgg aaccatactc gcaatacagc aatgttcagt ttccccaagt tcaaccacag    180
atttcctcgt catcctatta ttccaacctg ggtttctacc cccagcagcc tgaagagtgg    240
tactctcctg gaatatatga actcaggcgt atgccagctg agactctcta ccagggagaa    300
actgaggtag cagagatgcc tgtaacaaag aagccccgca tgggcgcgtc agcagggagg    360
atcaaagggg atgagctgtg tgttgtttgt ggagacagag cctctggata ccactataat    420
gcactgacct gtgaggggtg taaaggtttc ttcaggagaa gcattaccaa aaacgctgtg    480
tacaagtgta aaaacggggg caactgtgtg atggatatgt acatgcgaag aaagtgtcaa    540
gagtgtcgac taaggaaatg caaagagatg ggaatgttgg ctgaatgtat gtatacaggc    600
ttgttaactg aaattcagtg taaatctaag cgactgagaa aaaatgtgaa gcagcatgca    660
gatcagaccg tgaatgaaga cagtgaaggt cgtgacttgc gacaagtgac ctcgacaaca    720
aagtcatgca gggagaaaac tgaactcacc ccagatcaac agactcttct acattttatt    780
atggattcat ataacaaaca gaggatgcct caggaaataa caaataaaat tttaaaagaa    840
gaattcagtg cagaagaaaa ttttctcatt ttgacggaaa tggcaaccaa tcatgtacag    900
gttcttgtag aattcacaaa aaagctacca ggatttcaga ctttggacca tgaagaccag    960
attgctttgc tgaaagggtc tgcggttgaa gctatgttcc ttcgttcagc tgagattttc   1020
aataagaaac ttccgtctgg gcattctgac ctattggaag aaagaattcg aaatagtggt   1080
atctctgatg aatatataac acctatgttt agttttata aaagtattgg ggaactgaaa   1140
atgactcaag aggagtatgc tctgcttaca gcaattgtta tcctgtctcc agatagacaa   1200
tacataaagg atagagaggc agtagagaag cttcaggagc cacttcttga tgtgctacaa   1260
aagttgtgta agattcacca gcctgaaaat cctcaacact ttgcctgtct cctgggtcgc   1320
ctgactgaat tacggacatt caatcatcac cacgctgaga tgctgatgtc atggagagta   1380
aacgaccaca agtttacccc acttctctgt gaaatctggg acgtgcagtg a            1431
```

FIG. 4B

SEQ. ID NO. 2

| | |
|---|---:|
| MLVKPLPDSE EEGHDNQEAH QKYETMQCFA VSQPKSIKEE GEDLQSCLIC VARRVPMKER | 60 |
| PVLPSSESFT TRQDLQGKIT SLDTSTMRAA MKPGWEDLVR RCIQKFHAQH EGESVSYAKR | 120 |
| HHHEVLRQGL AFSQIYRFSL SDGTLVAAQT KSKLIRSQTT NEPQLVISLH MLHREQNVCV | 180 |
| MNPDLTGQTM GKPLNPISSN SPAHQALCSG NPGQDMTLSS NINFPINGPK EQMGMPMGRF | 240 |
| GGSGGMNHVS GMQATTPQGS NYALKMNSPS QSSPGMNPGQ PTSMLSPRHR MSPGVAGSPR | 300 |
| IPPSQFSPAG SLHSPVGVCS STGNSHSYTN SSLNALQALS EGHGVSLGSS LASPDLKMGN | 360 |
| LQNSPVNMNP PPLSKMGSLD SKDCFGLYGE PSEGTTGQAE SSCHPGEQKE TNDPNLPPAV | 420 |
| SSEPADGQSR LHDSKGQTKL LQLLTTKSDQ MEPSPLASSL SDTNKDSTGS LPGSGSTHGT | 480 |
| SLKEKHKILH RLLQDSSSPV DLAKLTAEAT GKDLSQESSS TAPGSEVTIK QEPVSPKKKE | 540 |
| NALLRYLLDK DDTKDIGLPE ITPKLERLDS KTDPASNTKL IAMKTEKEEM SFEPGDQPGS | 600 |
| ELDNLEEILD DLQNSQLPQL FPDTRPGAPA GSVDKQAIIN DLMQLTAENS PVTPVGAQKT | 660 |
| ALRISQSTFN NPRPGQLGRL LPNQNLPLDI TLQSPTGAGP FPPIRNSSPY SVIPQPGMMG | 720 |
| NQGMIGNQGN LGNSSTGMIG NSASRPTMPS GEWAPQSSAV RVTCAATTSA MNRPVQGGMI | 780 |
| RNPAASIPMR PSSQPGQRQT LQSQVMNIGP SELEMNMGGP QYSQQQAPPN QTAPWPESIL | 840 |
| PIDQASFASQ NRQPFGSSPD DLLCPHPAAE SPSDEGALLD QLYLALRNFD GLEEIDRALG | 900 |
| IPELVSQSQA VDPEQFSSQD SNIMLEQKAP VFPQQYASQA QMAQGSYSPM QDPNFHTMGQ | 960 |
| RPSYATLRMQ PRPGLRPTGL VQNQPNQLRL QLQHRLQAQQ NRQPLMNQIS NVSNVNLTLR | 1020 |
| PGVPTQAPIN AQMLAQRQRE ILNQHLRQRQ MHQQQQVQQR TLMMRGQGLN MTPSMVAPSG | 1080 |
| MPATMSNPRI PQANAQQFPF PPNYGISQQP DPGFTGATTP QSPLMSPRMA HTQSPMMQQS | 1140 |
| QANPAYQAPS DINGWAQGNM GGNSMFSQQS PPHFGQQANT SMYSNNMNIN VSMATNTGGM | 1200 |
| SSMNQMTGQI SMTSVTSVPT SGLSSMGPEQ VNDPALRGGN LFPNQLPGMD MIKQEGDTTR | 1260 |
| KYC | 1263 |

FIG. 4C

SEQ. ID NO. 3

```
   1 ggcggccgca gcctcggcta cagcttcggc ggcgaaggtc agcgccgacg gcagccggca
  61 cctgacggcg tgaccgaccc gagccgattt ctcttggatt tggctacaca cttatagatc
 121 ttctgcactg tttacaggca cagttgctga tatgtgttca agatgagtgg gatgggagaa
 181 aatacctctg accectccag ggcagagaca agaaagcgca aggaatgtcc tgaccaactt
 241 ggacccagcc ccaaaaggaa cactgaaaaa cgtaatcgtg aacaggaaaa taaatatata
 301 gaagaacttg cagagttgat ttttgcaaat tttaatgata tagacaactt taacttcaaa
 361 cctgacaaat gtgcaatctt aaaagaaact gtgaagcaaa ttcgtcagat caaagaacaa
 421 gagaaagcag cagctgccaa catagatgaa gtgcagaagt cagatgtatc ctctacaggg
 481 cagggtgtca tcgacaagga tgcgctgggg cctatgatgc ttgaggccct tgatgggttc
 541 ttctttgtag tgaacctgga aggcaacgtt gtgtttgtgt cagagaatgt gacacagtat
 601 ctaaggtata accaagaaga gctgatgaac aaaagtgtat atagcatctt gcatgttggg
 661 gaccacacgg aatttgtcaa aaacctgctg ccaaagtcta taggtaaatg ggggatcttg
 721 gtctggcgaa cctccgaggc ggaacagcca taccttcaat tgtcggatgc tggtaaaacc
 781 tttacctgat tcagaagagg agggtcatga taaccaggaa gctcatcaga aatatgaaac
 841 tatgcagtgc ttcgctgtct ctcaaccaaa gtccatcaaa gaagaaggag aagatttgca
 901 gtcctgcttg atttgcgtgg caagaagagt tcccatgaag gaaagaccag ttcttccctc
 961 atcagaaagt tttactactc gccaggatct ccaaggcaag atcacgtctc tggataccag
1021 caccatgaga gcagccatga accaggctg ggaggacctg gtaagaaggt gtattcagaa
1081 gttccatgcg cagcatgaag gagaatctgt gtcctatgct aagaggcatc atcatgaagt
1141 actgagacaa ggattggcat tcagtcaaat ctatcgtttt tccttgtctg atggcactct
1201 tgttgctgca caaacgaaga gcaaactcat ccgttctcag actactaatg aacctcaact
```

SEQ. ID NO. 4

FIG. 4D – 1

```
1261 tgtaatatct ttacatatgc ttcacagaga gcagaatgtg tgtgtgatga atccggatct
1321 gactggacaa acgatgggga agccactgaa tccaattagc tctaacagcc ctgcccatca
1381 ggccctgtgc agtgggaacc caggtcagga catgaccctc agtagcaata taaattttcc
1441 cataaatggc ccaaaggaac aaatgggcat gccatgggc aggtttggtg gttctggggg
1501 aatgaaccat gtgtcaggca tgcaagcaac cactcctcag ggtagtaact atgcactcaa
1561 aatgaacagc ccctcacaaa gcagccctgg catgaatcca ggacagccca cctccatgct
1621 ttcaccaagg catcgcatga gccctggagt ggctggcagc cctcgaatcc cacccagtca
1681 gtttccccct gcaggaagct tgcattcccc tgtgggagtt tgcagcagca caggaaatag
1741 ccatagttat accaacagct ccctcaatgc acttcaggcc ctcagcgagg ggcacggggt
1801 ctcattaggg tcatcgttgg cttcaccaga cctaaaaatg gcaatttgc aaaactcccc
1861 agttaatatg aatcctcccc cactcagcaa gatgggaagc ttggactcaa aagactgttt
1921 tggactatat ggggagccct ctgaaggtac aactggacaa gcagagagca gctgccatcc
1981 tggagagcaa aaggaaacaa atgacccaa cctgccccg gccgtgagca gtgagagagc
2041 tgacgggcag agcagactgc atgacagcaa agggcagacc aaactcctgc agctgctgac
2101 caccaaatct gatcagatgg agccctcgcc cttagccagc tctttgtcgg atacaaacaa
2161 agactccaca ggtagcttgc ctggttctgg gtctacacat ggaacctcgc tcaaggagaa
2221 gcataaaatt ttgcacagac tcttgcagga cagcagttcc cctgtggact tggccaagtt
2281 aacagcagaa gccacaggca aagacctgag ccaggagtcc agcagcacag ctcctggatc
2341 agaagtgact attaaacaag agccggtgag ccccaagaag aaagagaatg cactacttcg
2401 ctatttgcta gataaagatg atactaaaga tattggttta ccagaaataa cccccaaact
2461 tgagagactg gacagtaaga cagatcctgc cagtaacaca aaattaatag caatgaaaac
2521 tgagaaggag gagatgagct ttgagcctgg tgaccagcct ggcagtgagc tggacaactt
2581 ggaggagatt ttggatgatt tgcagaatag tcaattacca cagcttttcc cagacacgag
2641 gccaggcgcc cctgctggat cagttgacaa gcaagccatc atcaatgacc tcatgcaact
2701 cacagctgaa aacagccctg tcacacctgt tggagcccag aaaacagcac tgcgaatttc
2761 acagagcact tttaataacc cacgaccagg gcaactgggc aggttattgc caaaccagaa
```

FIG. 4D - 2

```
2821 tttaccactt gacatcacat tgcaaagccc aactggtgct ggacctttcc caccaatcag
2881 aaacagtagt ccctactcag tgatacctca gccaggaatg atgggtaatc aagggatgat
2941 aggaaaccaa ggaaatttag ggaacagtag cacaggaatg attggtaaca gtgcttctcg
3001 gcctactatg ccatctggag aatgggcacc gcagagttcg gctgtgagag tcacctgtgc
3061 tgctaccacc agtgccatga accggccagt ccaaggaggt atgattcgga acccagcagc
3121 cagcatcccc atgaggccca gcagccagcc tggccaaaga cagacgcttc agtctcaggt
3181 catgaatata gggccatctg aattagagat gaacatgggg ggacctcagt atagccaaca
3241 acaagctcct ccaaatcaga ctgccccatg gcctgaaagc atcctgccta tagaccaggc
3301 gtcttttgcc agccaaaaca ggcagccatt tggcagttct ccagatgact tgctatgtcc
3361 acatcctgca gctgagtctc cgagtgatga gggagctctc ctggaccagc tgtatctggc
3421 cttgcggaat tttgatggcc tggaggagat tgatagagcc ttaggaatac ccgaactggt
3481 cagccagagc caagcagtag atccagaaca gttctcaagt caggattcca acatcatgct
3541 ggagcagaag gcgcccgttt tcccacagca gtatgcatct caggcacaaa tgcccaggg
3601 tagctattct cccatgcaag atccaaactt tcacaccatg ggacagcggc ctagttatgc
3661 cacactccgt atgcagccca gaccgggcct caggcccacg ggcctagtgc agaaccagcc
3721 aaatcaacta agacttcaac ttcagcatcg cctccaagca cagcagaatc gccagccact
3781 tatgaatcaa atcagcaatg tttccaatgt gaacttgact ctgaggcctg gagtaccaac
3841 acaggcacct attaatgcac agatgctggc ccagagacag agggaaatcc tgaaccagca
3901 tcttcgacag agacaaatgc atcagcaaca gcaagttcag caacgaactt tgatgatgag
3961 aggacaaggg ttgaatatga caccaagcat ggtggctcct agtggtatgc agcaactat
4021 gagcaaccct cggattcccc aggcaaatgc acagcagttt ccatttcctc caaactacgg
4081 aataagtcag caacctgatc caggctttac tggggctacg actccccaga gcccacttat
4141 gtcaccccga atggcacata cacagagtcc catgatgcaa cagtctcagg ccaacccagc
4201 ctatcaggcc ccctccgaca taaatggatg ggcgcagggg aacatgggcg gaaacagcat
```

FIG. 4D - 3

```
4261 gttttcccag cagtccccac cacactttgg gcagcaagca aacaccagca tgtacagtaa
4321 caacatgaac atcaatgtgt ccatggcgac caacacaggt ggcatgagca gcatgaacca
4381 gatgacagga cagatcagca tgacctcagt gacctccgtg cctacgtcag ggctgtcctc
4441 catgggtccc gagcaggtta atgatcctgc tctgagggga ggcaacctgt tcccaaacca
4501 gctgcctgga atggatatga ttaagcagga gggagacaca acacggaaat attgctgaca
4561 ctgctgaagc cagttgcttc ttcagctgac cgggctcact tgctcaaaac acttccagtc
4621 tggagagctg tgtctatttg tttcaaccca actgacctgc cagccggttc tgctagagca
4681 gacaggcctg gccctggttc ccagggtggc gtccactcgg ctgtggcagg aggagctgcc
4741 tcttctcttg acagtctgaa gctcgcatcc agacagtcgc tcagtctgtt cactgcattc
4801 accttagtgc aacttagatc tctcctgcaa agtaaatgt tgacaggcaa atttcatacc
4861 catgtcagat tgaatgtatt taaatgtatg tatttaagga gaaccatgct cttgttctgt
4921 tcctgttcgg ttccagacac tggtttcttg ctttgttttc cctggctaac agtctagtgc
4981 aaaagattaa gattttatct gggggaaaga aaagaatttt ttaaaaatt aaactaaaga
5041 tgttttaagc taaagcctga atttgggatg gaagcaggac agacaccgtg gacagcgctg
5101 tatttacaga cacacccagt gcgtgaagac caacaaagtc acagtcgtat ctctagaaag
5161 ctctaaagac catgttggaa agagtctcca gttactgaac agatgaaaag gagcctgtga
5221 gagggctgtt aacattagca aatatttttt ccttgttttt tctttgttaa aaccaaactg
5281 gttcacctga atcatgaatt gagaagaaat aattttcatt tctaaattaa gtcccttta
5341 gtttgatcag acagcttgaa tcagcatctc ttcttccctg tcagcctgac tcttcccttc
5401 ccctctctca ttccccatac tccctatttt cattcctttt ttaaaaaata atataagcta
5461 cagaaccag gtaagccctt tatttcctta aatgttttgc cagccactta ccaattgcta
5521 agtattgaat ttcagaaaaa aaaatgcat ttactggcaa ggagaagagc aaagttaagg
5581 cttgatacca atcgagctaa ggatacctgc tttggaagca tgtttattct gttccccagc
5641 aactctggcc tccaaaatgg gagaaaacgc cagtgtgttt aaattgatag cagatatcac
5701 gacagattta acctctgcca tgtgttttttt attttgtttt ttagcagtgc tgactaagcc
5761 gaagttttgt aaggtacata aaatccaatt tatatgtaaa caagcaataa tttaagttga
5821 gaacttatgt gttttaattg tataattttt gtgaggtata catattgtgg aattgactca
```

FIG. 4D - 4

```
5881 aaaatgaggt actccagtat taaattagat atcttcatag caatgtctcc taaaggtgtt
5941 ttgtaaagga tatcaatgcc ttgattagac ctaatttgta gacttaagac tttttatttt
6001 ctaaaccttg tgattctgct tataagtcat ttatctaatc tatatgatat gcagccgctg
6061 taggaaccaa ttcttgattt ttatatgttt atattctttc ttaatgaacc ttagaaagac
6121 tacatgttac taagcaggcc acttttatgg ttgttttt
```

FIG. 4D - 5

NR1H4 NUCLEAR RECEPTOR BINDING COMPOUNDS

FIELD OF THE INVENTION

The present invention relates to compounds that bind to the NR1H4 nuclear receptor and methods of treating diseases or pathological conditions influenced by NR1H4.

BACKGROUND OF THE INVENTION

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often simple molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known (Escriva, H. et al., Ligand binding was acquired during evolution of nuclear receptors, PNAS, 94, 6803–6808, 1997). Orphan receptors may be indicative of unknown signaling pathways in the cell or may be nuclear receptors that function without ligand activation. The activation of transcription by some of these orphan receptors may occur in the absence of an exogenous ligand and/or through signal transduction pathways originating from the cell surface (Mangelsdorf, D. J. et al., The nuclear receptor superfamily: the second decade, Cell 83, 835–839, 1995).

In general, three functional domains have been defined in NRs. An amino terminal domain is believed to have some regulatory function. A DNA-binding domain hereinafter referred to as "DBD" usually comprises two zinc finger elements and recognizes a specific Hormone Responsive Element (hereinafter referred to as "HRE") within the promoters of responsive genes. Specific amino acid residues in the "DBD" have been shown to confer DNA sequence binding specificity (Schena, M. & Yamamoto, K. R., Mammalian Glucocorticoid Receptor Derivatives Enhance Transcription in Yeast, Science, 241:965–967, 1988). A ligand-binding-domain (hereinafter referred to as "LBD") is at the carboxy-terminal region of known NRs. In the absence of hormone, the LBD appears to interfere with the interaction of the DBD with its HRE. Hormone binding seems to result in a conformational change in the NR, and thus, opens this interference (Brzozowski et al., Molecular basis of agonism and antagonism in the oestogen receptor, Nature, 389, 753–758, 1997; Wagner et al., A structural role for hormone in the thyroid hormone receptor, Nature, 378, 690–697, 1995). A NR without the LBD constitutively activates transcription, but at a low level.

Coactivators or transcriptional activators are proposed to bridge between sequence specific transcription factors, the basal transcription machinery, and in addition, to influence the chromatin structure of a target cell. Several proteins like SRC-1, ACTR, and Grip1 interact with NRs in a ligand enhanced manner (Heery et al., A signature motif in transcriptional coactivators mediates binding to nuclear receptors, Nature, 387, 733–736; Heinzel et al., A complex containing N-CoR, mSin3 and histone deacetylase mediates transcriptional repression, Nature 387, 43–47, 1997). Furthermore, the physical interaction with negative receptor-interacting proteins or corepressors has been demonstrated (Xu et al., Coactivator and Corepressor complexes in nuclear receptor function, Curr Opin Genet Dev, 9 (2), 140–147, 1999).

Nuclear receptor modulators like steroid hormones affect the growth and function of specific cells by binding to intracellular receptors and forming nuclear receptor-ligand complexes. Nuclear receptor-hormone complexes then interact with a HRE in the control region of specific genes and alter specific gene expression.

The Farnesoid X Receptor alpha (hereinafter to as "FXR" and also often referred to as "NR1H4" when referring to the human receptor) is a prototypical type 2 nuclear receptor which activates genes upon binding to promoter region of target genes in a heterodimeric fashion with Retinoid X Receptor (hereinafter referred to as "RXR") (Forman et al., Cell, 81, 687–93, 1995). The relevant physiological ligands of NR1H4 seem to be bile acids (Makishima et al., Science, 284, 1362–65, 1999; Parks et al., Science, 284, 1365–68, 1999). The most potent is chenodeoxycholic acid, which regulates the expression of several genes that participate in bile acid homeostasis. Famesoid, originally described to activate the rat ortholog at high concentration does not activate the human or mouse receptor. FXR is expressed in the liver, small intestine, colon, ovary, adrenal gland and kidney. Like FXRα, NR1H4 is involved in intracrine signaling.

FXR is proposed to be a nuclear bile acid sensor. As a result, it modulates both, the synthetic output of bile acids in the liver and their recycling in the intestine (by regulating bile acid binding proteins). Upon activation (e.g. binding of chenodeoxycholic acid) it influences the conversion of dietary cholesterol into bile acids by inhibiting the transcription of key genes which are involved in bile acid synthesis such as CYP7A1. This seems to be a major mechanism of feedback regulation onto bile acid synthesis.

The synthetic compounds, 1,1-bisphosphonate esters, appear to display a number of similar activities to the two identified prototypes of natural FXR agonists, farnesol, and chenodeoxycholc acid. Like farnesol, the 1,1-bisphosphonate esters increase the rate of 3-Hydroxy-3-methylglutaryl-CoA (HMG-CoA) reductase degradation and like bile acids they induce the expression of the intestinal bile acid binding protein (hereinafter referred to as "I-BABP") and repress the cholesterol 7 α-hydroxylase gene. Certain 1,1-bisphosphonate esters also bind to FXR (Niesor et al., Curr Pharm Des,7(4):231–59, 2001). That means that activation of FXR could lead to opposing effects (lowering the rate of cholesterol synthesis by increasing degradation of HMG-CoA reductase and increasing the cholesterol pool by inhibition of cholesterol degradation into bile acids). The FXR agonist, chenodeoxycholic acid, does not change cholesterol and lipoprotein levels significantly in patients, although a repression of bile acid synthesis as well as a decreased HMG-CoA reductase activity was observed (Einarsson et al., Hepatology, 33(5), 1189–93, 2001) confirming that cellular cholesterol synthesis and degradation are controlled by numerous regulatory loops including the coordinate regulation of HMGCoA reductase and cholesterol 7α-hydroxylase and that compounds modulating FXR acitvity might have different effects on blood lipid parameters.

In the course of functional analysis of certain 1,1-bisphosphonate esters, it was shown that these compounds which are known to bind to FXR also induce apoptosis in a variety of cell types, similar to the isporenoids farnesol and geranylgeraniol which are also known as weak FXR binders (Flach et al., Biochem Biophys Res Com, 270, 240–46, 2000).

To date only very few compounds have been described which bind the NR1H4 receptor, and thus, show utility for treating diseases or conditions which are due to or influenced by this nuclear receptor (Maloney at al., J Med Chem, 10; 43(16): 2971–2974, 2000).

It is an object of the present invention to provide for a novel NR1H4 binding compound. It was also an object of the present invention to provide for compounds which, by means of binding the NR1H4 receptor, act as an agonist or antagonist of said receptor, and thus, show utility for treating diseases or conditions which are due to or influenced by said nuclear receptor.

It is a further object of the invention to provide for compounds which may be used for the manufacture of a medicament for the treatment of cholesterol associated conditions or diseases. In a preferred embodiment of the invention it was an object of the invention to provide for cholesterol lowering or cholestatic compounds. It was also an object of the invention to provide for compounds may be used for the manufacture of antitumor medicaments.

SUMMARY OF THE INVENTION

The present invention provides, inter alia, novel NR1H4 nuclear receptor protein binding compounds according to the general formula (I) shown below. These compounds are also binders of mammalian homologues of the receptor. Further the object of the invention is solved by providing for, amongst the NR1H4 nuclear receptor protein binding, compounds according to the general formula (I) which act as agonists and compounds which act as antagonists of the human FXR receptor or a mammalian homologue thereof.

The invention provides for FXR agonists which may be used for the treatment of cholesterol associated conditions or diseases. In a preferred embodiment of the invention cholesterol lowering or cholestatic compounds are disclosed. The compounds according to the invention may be used for manufacture of antitumor medicaments and/or for the treatment of diseases such as cancer.

The foregoing merely summarizes certain aspects of the present invention and is not intended, nor should it be construed, to limit the invention in any manner. All patents and other publications recited herein are hereby incorporated by reference in their entirety.

BRIEF DESCRIPTION OF THE DRAWINGS

The various novel features of this invention, along with the foregoing and other objects as well as the invention itself may be more fully understood from the following description when read in conjunction with the accompanying drawings.

FIG. 4A shows SEQ ID No. 1 which is a protein sequence of the FRX protein, a portion of which can be used for cloning.

FIG. 4B shows SEQ ID NO. 2 which is the mRNA sequence encoding the FRX protein.

FIG. 4C shows SEQ ID NO. 3 which shows the protein sequence of TIF2 (Acc. No.: XM 011633 RefSeq DB).

FIG. 4D shows SEQ ID NO. 4 which is respective mRNA sequence corresponding to the TIF2 protein.

DETAILED DESCRIPTION OF THE INVENTION

Figures 1, 1A:
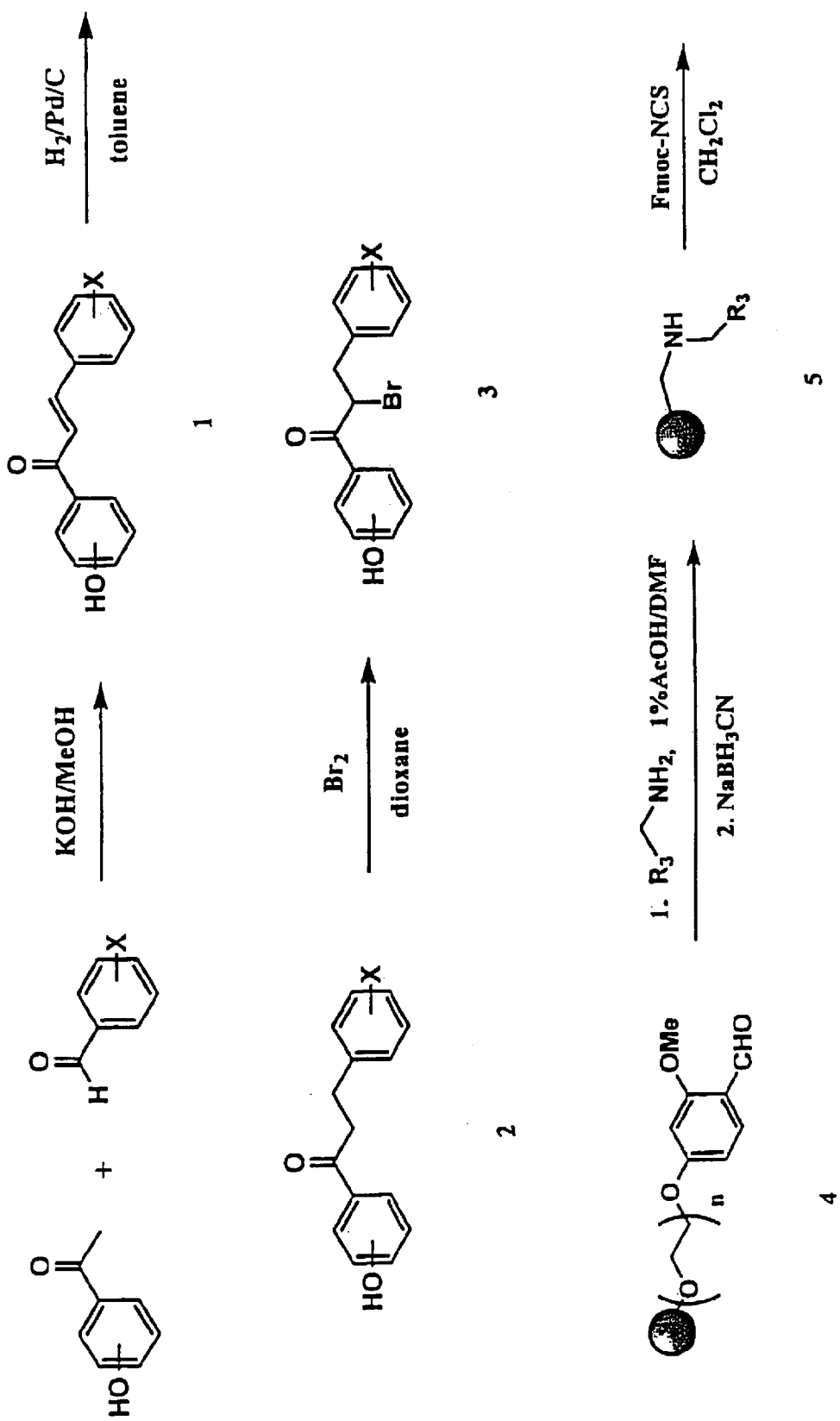
FIGS. 1A and 1B show the synthesis of the compounds of the invention described in Example 2.

The invention provides for a compound including resolved diastereoisomers and enantiomers, and tautomers, pharmaceutical acceptable salts or solvates thereof (hereinafter also referred to as the "compounds according to the invention"), having the following formula (1):

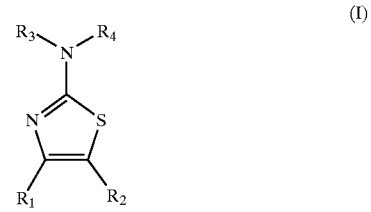

wherein $R_1$ and $R_2$ are independently selected from the group consisting of $C_1$ to $C_8$ alkyl, $C_1$ to $C_8$ substituted alkyl, phenyl, substituted phenyl, $C_7$ to $C_{12}$ phenylalkyl, $C_7$ to $C_{12}$ substituted phenylalkyl, heterocyclic ring, substituted heterocyclic ring, heteroaryl, and substituted heteroaryl; and $R_3$ and $R_4$ are independently selected from the group consisting of hydrogen, $C_1$ to $C_8$ alkyl, $C_1$ to $C_8$ substituted alkyl, phenyl, substituted phenyl, $C_7$ to $C_{12}$ phenylalkyl, $C_7$ to $C_{12}$ substituted phenylalkyl, naphthyl, substituted naphthyl, $C_1$ to $C_8$ alkanesulfonyl, $C_1$ to $C_8$ substituted alkanesulfonyl, benzenesulfonyl, substituted benzenesulfonyl, $C_1$ to $C_8$ acyl, and $C_1$ to $C_8$ substituted acyl; where $R_3$ and $R_4$ may be taken together with nitrogen to form a heterocycle or substituted heterocycle or a heteroaryl or substituted heteroaryl ring.

In one embodiment of the present invention, $R_1$ and $R_2$ in formula (I) are independently selected from the group consisting of phenyl, substituted phenyl, $C_7$ to $C_{12}$ phenylalkyl, $C_7$ to $C_{12}$ substituted phenylalkyl, heteroaryl, and substituted heteroaryl; $R_3$ and $R_4$ are independently selected from the group consisting of hydrogen, $C_1$ to $C_8$ alkyl, $C_1$ to $C_8$ substituted alkyl, substituted phenyl, $C_7$ to $C_{12}$ phenylalkyl, $C_7$ to $C_{12}$ substituted phenylalkyl, substituted naphthyl, $C_1$ to $C_8$ substituted alkanesulfonyl, and substituted benzenesulfonyl; where $R_3$ and $R_4$ may be taken together with nitrogen to form a heterocycle or a substituted heterocycle or a heteroaryl or a substituted heteroaryl ring.

In a more preferred embodiment of the present invention, $R_1$ and $R_2$ are independently selected from the group consisting of phenyl, substituted phenyl, $C_7$ to $C_{12}$ phenylalkyl, $C_7$ to $C_{12}$ substituted phenylalkyl, heteroaryl, and substituted heteroaryl; $R_3$ and $R_4$ are independently selected from the group consisting of hydrogen, $C_1$ to $C_8$ substituted alkyl, substituted phenyl, $C_7$ to $C_{12}$ substituted phenylalkyl, substituted naphthyl, $C_1$ to $C_8$ substituted alkanesulfonyl, and substituted benzenesulfonyl, wherein at least one of the mentioned above groups is substituted with carboxylic acid functionality as shown in formula (II) below:

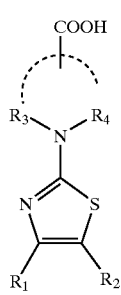

(II)

where $R_3$ and $R_4$ may be taken together with nitrogen to form a heterocycle or a substituted heterocycle or a heteroaryl or substituted heteroaryl ring, also substituted with carboxylic acid functionality.

In a more preferred embodiment of the invention compounds are claimed, or pharmaceutical acceptable salts or solvates thereof, wherein $R_1$ and $R_2$ are independently selected from the group consisting of phenyl, substituted phenyl, $C_7$ to $C_{12}$ phenylalkyl, $C_7$ to $C_{12}$ substituted phenylalkyl, heteroaryl, and substituted heteroaryl; $R_3$ is hydrogen, $C_1$ to $C_8$ alkyl, $C_1$ to $C_8$ substituted alkyl, $C_1$ to $C_8$ acyl, $C_1$ to $C_8$ substituted acyl, $C_1$ to $C_8$ alkanesulfonyl, $C_1$ to $C_8$ substituted alkanesulfonyl, benzenesulfonyl, and substituted benzenesulfonyl; and $R_4$ is one of the following structural formulas:

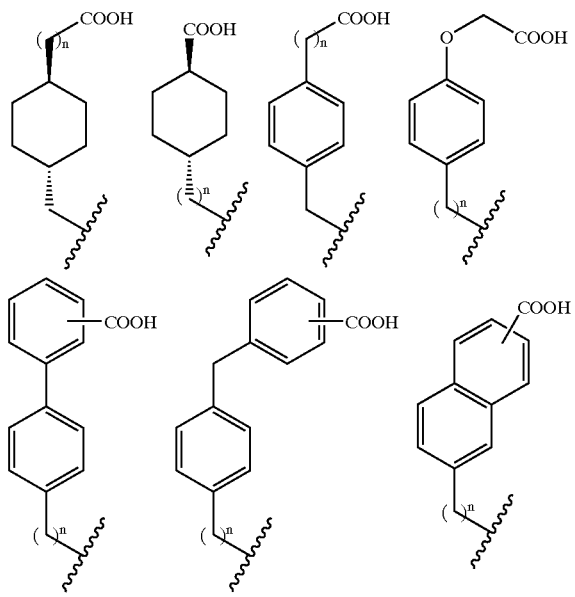

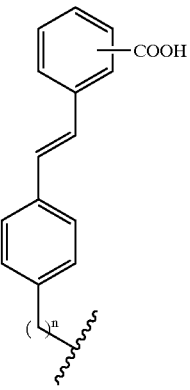

n = 0–3 wherein n is an integer from 0 to 3. The symbol:

indicates the point of attachment of $R_4$ where $R_4$ is covalently bonded to Formula (I).

In a more preferred embodiment of the invention, there are provided compounds including resolved diastereoisomers and enantiomers, and tautomers, pharmaceutical acceptable salts or solvates thereof, wherein $R_1$ and $R_2$ are independently selected from the group consisting of substituted phenyl, $C_7$ to $C_{12}$ substituted phenylalkyl, and substituted heteroaryl, where preferred substituents are taken from hydrogen, halogen, hydroxy or alkoxy groups; $R_3$ is hydrogen, $C_1$ to $C_8$ alkyl, $C_1$ to $C_8$ substituted alkyl, $C_1$ to $C_8$ acyl, and $C_1$ to $C_8$ substituted acyl; and $R_4$ is one of the structures set forth above.

A particularly preferred compound which may act as agonist of NR1H4 is shown in formula (III) below. The inventors have been able to demonstrate that the compound according to formula (III) has a low effective binding concentration at FXR with an $EC_{50}$ of 0.2 µM wherein the $EC_{50}$ reflects the half-maximal effective concentration, and which is higher than the $EC_{50}$ of 0.015 µM for the published FXR agonist GW4064 (B. Goodwin et al., Molecular Cell 6, 517–526, 2000).

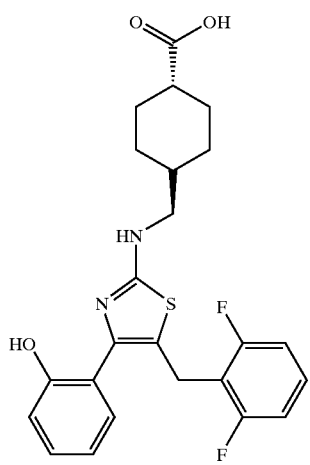

(III)

The inventors have also found the compounds according to formulas (IV), (V) and (VI) shown below to be active as agonist of the NR1H4 human nuclear receptor (see figures for details).

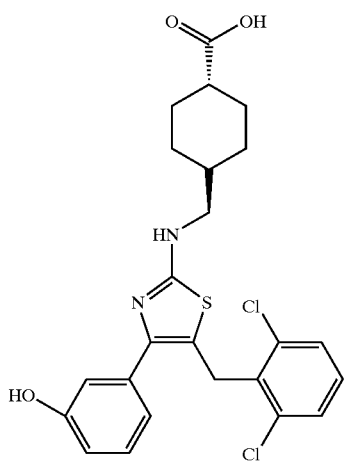

(IV)

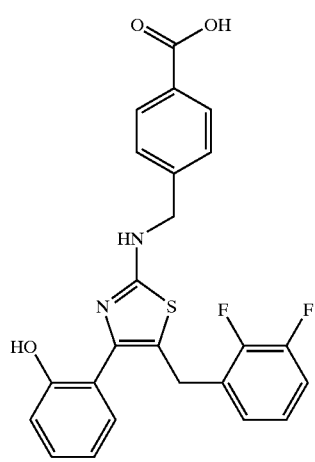

(V)

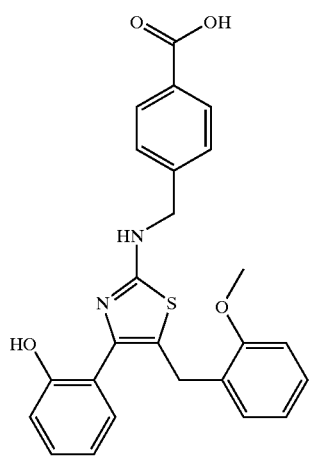

(VI)

The inventors have identified the compounds as well as the general structure capable of effectively binding FXR.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid, which is in a mixture with the finely divided active component. In tablets, the active compound or combination of active compounds is mixed with the carrier having the necessary binding properties in suitable proportions and compacted in the shape and size desired.

For preparing a pharmaceutical composition in the form of suppositories, a low-melting wax such as a mixture of fatty acid glycerides and cocoa butter is first melted and the active ingredient or combination of active ingredients is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound(s) with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component(s) in the desired solvent system, and then passing the resulting solution through a membrane filter to sterilize it or, alternatively, by dissolving the sterile compound in a previously sterilized solvent under sterile conditions.

The term "halogen" refers to the fluoro, chloro, bromo or iodo atoms. There can be one or more halogen, which are the same or different. Preferred halogens are chloro and fluoro.

The term "$C_1$ to $C_8$ alkyl" denotes such radicals as methyl, ethyl, n-propyl, isopropyl, n-butyl, iso-butyl, sec-butyl, tert-butyl, amyl, tert-amyl, hexyl, n-heptyl, 2-heptyl, 3-heptyl, 4-heptyl, 2-methyl-1-hexyl, 2-methyl-2-hexyl, 2-methyl-3-hexyl, n-octyl and the like.

The term "$C_1$ to $C_8$ substituted alkyl" denotes that the above $C_1$ to $C_8$ alkyl groups are substituted by one or more, and preferably one or two, halogen, hydroxy, protected hydroxy, oxo, protected oxo, $C_3$ to $C_7$ cycloalkyl, phenyl, naphthyl, amino, protected amino, monosubstituted amino, protected monosubstituted amino, disubstituted amino, guanidino, protected guanidino, heterocyclic ring, substituted heterocyclic ring, $C_1$ to $C_8$ alkoxy, $C_1$ to $C_8$ acyl, $C_1$ to $C_8$ acyloxy, nitro, carboxy, protected carboxy, carbamoyl, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, 4-carboxybutyl, 5-carboxypentyl, 6-carboxyhexyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_8$ alkyl, $C_1$ to $C_8$ substituted alkyl, $C_1$ to $C_8$ alkoxy, $C_1$ to $C_8$ substituted alkoxy, $C_1$ to $C_8$ acyl, $C_1$ to $C_8$ substituted acyl, $C_1$ to $C_8$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N—($C_1$ to $C_6$ alkyl)carboxamide, protected N—($C_1$ to $C_6$ alkyl) carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, wherein the phenyl is substituted or unsubstituted, such that, for example, a biphenyl results.

Examples of the term "substituted phenyl" includes a mono- or di(halo)phenyl group such as 2, 3 or 4-chlorophenyl, 2,6-difluorophenyl, 2,3-difluorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(iso-propyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "$C_7$ to $C_{12}$ phenylalkyl" denotes a $C_1$ to $C_6$ alkyl group substituted at any position by a phenyl, substituted phenyl, heteroaryl or substituted heteroaryl. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, monosubstituted amino, protected monosubstituted amino, disubstituted amino, guanidino, protected guanidino, heterocyclic ring, substituted heterocyclic ring, $C_1$ to $C_8$ alkyl, $C_1$ to $C_8$ substituted alkyl, $C_1$ to $C_8$ alkoxy, $C_1$ to $C_8$ substituted alkoxy, $C_1$ to $C_8$ acyl, $C_1$ to $C_8$ substituted acyl, $C_1$ to $C_8$ acyloxy, nitro, carboxy, protected carboxy, carbamoyl, carboxamide, protected carboxamide, N—($C_1$ to $C_6$ alkyl) carboxamide, protected N—($C_1$ to $C_6$ alkyl)carboxamide, N,N—($C_1$ to $C_6$ dialkyl)carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_8$ alkyl, $C_1$ to $C_8$ substituted alkyl, $C_1$ to $C_8$ alkoxy, $C_1$ to $C_8$ substituted alkoxy, $C_1$ to $C_8$ acyl, $C_1$ to $C_8$ substitute acyl, $C_1$ to $C_8$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl) carboxamide, N,N-di($C_1$ to $C_6$ alkyl)carboxamide, trifluoromethyl, N—(($C_1$ to $C_6$ alkyl)sulfonyl)amino, N-(phenylsulfonyl) amino, cyclic $C_2$ to $C_8$ alkylene or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-hydroxyphenylmethyl, 3-hydroxyphenylmethyl, 2-methoxyphenylmethyl, 3-methoxyphenylmethyl, 2,6-difluorophenylmethyl, 2,3-difluorophenylmethyl, 2,6-dichlorophenylmethyl, 2,3-dichlorophenylmethyl, 3,5-dichlorophenylmethyl, 2-hydroxyphenylethyl, 3-hydroxyphenylethyl, 2-methoxyphenylethyl, 3-methoxyphenylethyl, 2,6-difluorophenylethyl, 2,3-difluorophenylethyl, 2,6-dichlorophenylethyl, 2,3-dichlorophenylethyl, 3,5-dichlorophenylmethyl 2-phenyl-1-chloroethyl, 2-(4-methoxyphenyl)ethyl, 4-(2,6-dihydroxy phenyl)n-hexyl, 2-(5-cyano-3-methoxyphenyl) n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl and the like.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophen-yl, hexamethyleneimino and heptamethyleneimino.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_8$ alkyl, $C_1$ to $C_8$ alkoxy, $C_1$ to $C_8$ substituted alkoxy, $C_1$ to $C_8$ acyl, $C_1$ to $C_8$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino carboxamide, protected carboxamide, N—($C_1$ to $C_{12}$ alkyl) carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl) amino, heterocycle or substituted heterocycle groups.

The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, thiopheno, oxazolo, isoxazolo, phthalimido, thiazolo and the like.

The term "substituted heteroaryl" means the above-described heteroaryl is substituted with, for example, one or more, and preferably one or two substituents which are the same or different which substituents can be halogen, hydroxy, protected hydroxy, cyano, nitro, $C_1$ to $C_8$ alkyl, $C_1$ to $C_8$ alkoxy, $C_1$ to $C_8$ substituted alkoxy, $C_1$ to $C_8$ acyl, $C_1$ to $C_8$ substituted acyl, $C_1$ to $C_8$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino or N-(phenylsulfonyl) amino groups.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_8$ alkyl, $C_1$ to $C_8$ alkoxy, $C_1$ to $C_8$ acyl, $C_1$ to $C_8$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino or N-(phenylsulfonyl)amino.

Examples of the term "substituted naphthyl" includes a mono or di(halo)naphthyl group such as 1, 2, 3, 4, 5, 6, 7 or 8-chloronaphthyl, 2,6-dichloronaphthyl, 2,5-dichloronaphthyl, 3,4-dichloronaphthyl, 1, 2, 3, 4, 5, 6, 7 or 8-bromonaphthyl, 3, 4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2, 4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy) naphthyl group, for example, 2, 6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy) naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2, 4-di(-protected carboxy) naphthyl; a mono- or di(hydroxymethyl)naphthyl or (protected hydroxymethyl)naphthyl such as 1, 2, 3, 4, 5, 6, 7 or 8-(protected hydroxymethyl)naphthyl or 3, 4-di (hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)naphthyl such as 2, 3, or 4-(aminomethyl) naphthyl or 2,4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

As outlined above $R_3$ and $R_4$ may be taken together with nitrogen to form a heterocycle or substituted heterocycle of the following kind aziridine, azetidine, pyrrolidine, 3-methylpyrrolidine, 3-aminopyrrolidine, 3-hydroxypyrrolidine, pyrazolidine, imidazolidine, piperidine, 2-methylpiperidine, 4-carboxypiperidine, 4-(carboxymethyl)piperidine, piperazine, morpholine, azepine, and tetrahydroisoquinoline.

The term "$C_1$ to $C_8$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "$C_1$ to $C_8$ substituted acyl" denotes the acyl group substituted by one or more, and preferably one or two, halogen, hydroxy, protected hydroxy, oxo, protected oxo, cyclohexyl, naphthyl, amino, protected amino, monosubstituted amino, protected monosubstituted amino, disubstituted amino, guanidino, heterocyclic ring, substituted heterocyclic ring, imidazolyl, indolyl, pyrrolidinyl, $C_1$ to $C_8$ alkoxy, $C_1$ to $C_8$ acyl, $C_1$ to $C_8$ acyloxy, nitro, $C_1$ to $C_8$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted acyl groups may be substituted once or more, and preferably once or twice, with the same or with different substituents.

Examples of $C_1$ to $C_8$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl and the like.

The term "$C_1$ to $C_8$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_8$ substituted alkoxy" means the alkyl portion of the alkoxy can be substituted in the same manner as in relation to $C_1$ to $C_8$ substituted alkyl.

The term "$C_1$ to $C_8$ substituted aminoacyl" denotes the acyl group substituted by one or more, and preferably one or two, halogen, hydroxy, protected hydroxy, oxo, protected oxo, cyclohexyl, naphthyl, amino, protected amino, monosubstituted amino, protected monosubstituted amino, disubstituted amino, guanidino, heterocyclic ring, substituted heterocyclic ring, imidazolyl, indolyl, pyrrolidinyl, $C_1$ to $C_8$ alkoxy, $C_1$ to $C_8$ acyl, $C_1$ to $C_8$ acyloxy, nitro, $C_1$ to $C_8$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, cyano, methylsulfonylamino, thiol, $C_1$ to $C_6$ alkylthio or $C_1$ to $C_6$ alkylsulfonyl groups. The substituted acyl groups may be substituted once or more, and preferably once or twice, with the same or with different substituents.

This invention provides a pharmaceutical composition comprising an effective amount of a compound according to the invention. Such compositions can be administered by various routes, for example oral, rectal, subcutaneous, intramuscular, intravenous or intracerebral. The preferred route of administration would be oral at daily doses of the compound for adult human treatment of about 0.01–5000 mg, preferably 1–1500 mg per day. The appropriate dose may be administered in a single dose or as divided doses presented at appropriate intervals for example as two, three four or more subdoses per day.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

In particular, the invention relates to compounds as described above wherein the compounds are capable of binding the NR1H4 receptor protein or a portion thereof according to SEQ ID NOS 1–4 shown in FIGS. 4A–4D, respectively, or a mammalian homologue thereof. The claimed compound can bind to the NR1H4 receptor protein or a portion thereof in a mixture comprising 10–200 ng of NR1H4 receptor protein or a portion thereof, preferably the ligand binding domain, 20 mM Tris/HCl at pH 7.9; 60 mM KCl; 5 mM $MgCl_2$; 160 ng/$\mu$l BSA in a total volume of preferably about 25 $\mu$l.

A mammalian receptor protein homologue of the protein according to SEQ ID NO. 1 shown in FIG. 4A as used herein is a protein that performs substantially the same function as NR1H4 does in humans and shares at least 40% sequence identity at the amino acid level, preferably 50% sequence identity at the amino acid level more preferably 65% sequence identity at the amino acid level, even more preferably 75% sequence identity at the amino acid level and most preferably over 85% sequence identity at the amino acid level.

The invention in particular concerns a method for prevention or treatment of a NR1H4 receptor protein- or NR1H4 receptor protein homologue-mediated disease or condition in a mammal comprising administration of a therapeutically effective amount of a compound according to the invention wherein the prevention or treatment is directly or indirectly accomplished through the binding of a compound according to the invention to the NR1H4 receptor protein or to the NR1H4 receptor protein homologue.

The term mediated herein means that the physiological pathway in which the NR1H4 receptor protein acts is either directly or indirectly involved in the disease or condition to be treated or prevented. In the case where it is indirectly involved it could be that, e.g. modulating the activity of NR1H4 by a compound according to the invention influences a parameter which has a beneficial effect on a disease or a condition. One such example is that modulation of NR1H4 activity leads to decreased levels of serum cholesterol or certain lipoproteins, which, in turn, have a beneficial effect on the prevention and treatment of artherosclerosis. Herein a condition is a physiological or phenotypic state which is desirably altered. One such example would be obesity which is not necessarily medically harmful but nonetheless a non desirable phenotypic condition. In a preferred embodiment of the invention the method for prevention or treatment of a NR1H4 receptor protein mediated disease or condition is applied to a human. This may be male or female.

Pharmaceutical compositions generally are administered in an amount effective for treatment or prophylaxis of a specific condition or conditions. Initial dosing in a human is accompanied by clinical monitoring of symptoms, such symptoms being determined for the selected condition. In general, the compositions are administered in an amount of active agent of at least about 100 $\mu$g/kg body weight. In most cases they will be administered in one or more doses in an amount not in excess of about 20 mg/kg body weight per day. Preferably, in most cases, the dose is from about 100 $\mu$g/kg to about 5 mg/kg body weight, daily.

For administration particularly to mammals, and particularly humans, it is expected that the daily dosage level of active agent will be 0.1 mg/kg to 10 mg/kg and typically around 1 mg/kg.

By "therapeutically effective amount" is meant a symptom-alleviating or symptom-reducing amount, a cholesterol-reducing amount, a fatty acid absorption blocking amount, a protein and/or carbohydrate digestion-blocking amount and/or a de novo cholesterol biosynthesis-blocking amount of a compound according to the invention. The term "blocking" as used herein means either total blockage or partial blockage.

FXR is proposed to be a bile acid sensor. As a result, it modulates both the synthetic output of bile acids in the liver and their recycling in the intestine, by regulating bile acid binding proteins. In one embodiment of the invention the invention concerns a method for regulating bile transport in a mammal, in a preferred embodiment a human, which comprises activating the NR1H4 receptor with a therapeutically effective amount of a compound according to the invention.

Likewise the invention concerns a method of treating in mammal a disease which is affected by cholesterol, triglyceride, or bile acid levels comprising administering to a mammal in need of such treatment a therapeutically effective amount of a compound according to the invention.

Accordingly, the compounds according to the invention may also be used as a method of prevention or treatment of mammalian atherosclerosis, gallstone disease, lipid disorders, obesity or cardiovascular disorders such as coronary heart disease or stroke.

The invention further concerns a method of blocking fatty acid absorption in the intestine of a mammal comprising administering to the mammal a therapeutically effective amount of a compound according to the invention. The invention may also be used to treat obesity in a mammal, particularly in humans.

FXR alpha is a prototypical type 2 nuclear receptor which activates genes upon binding to the promoter region of target genes in a heterodimeric fashion with RXR. The relevant physiological ligands of NR1H4 are bile acids. The present compounds according to the invention have been demonstrated to have high binding efficacy binding coefficients measured as IC50 in the range 400 nM to 1000 nM as well as agonistic and/or antagonistic properties. Consequently they may be applied to regulate genes that participate in bile acid homeostasis as well as other downstream regulated genes. Examples of such genes are, but are not limited to, genes encoding proteins or factors involved directly or indirectly in lipid absorption, cholesterol biosynthesis, cholesterol transport or binding, bile acid transport or binding, proteolysis, amino acid metabolism, glucose biosynthesis, protein translation, electron transport, and hepatic fatty acid metabolism. FXR often functions in vivo as a heterodimer with the RXR. Published FXR agonists such as the Glaxo SmithKline compound "GW 4064" are known to influence the regulation of various liver genes. Examples of known agonists are showin in Table 1 below.

TABLE 1

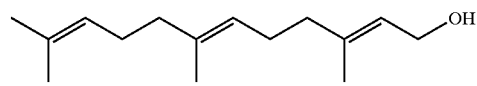

Farnesol

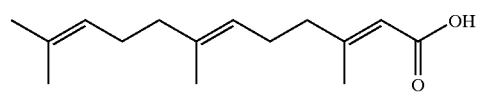

Farnesoic acid

TABLE 1-continued

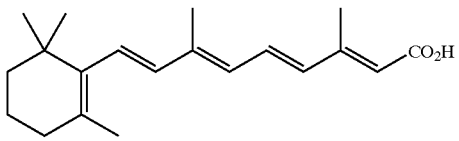

All trans-Retinoic acid

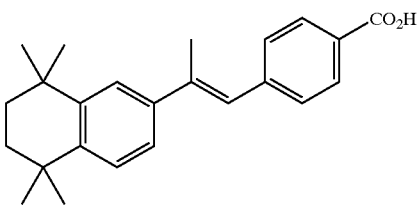

TTNPB

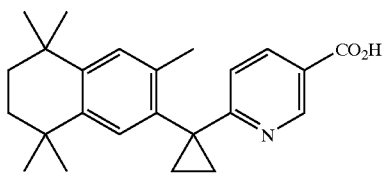

LG 268

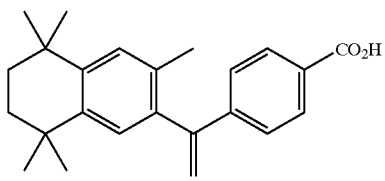

LG 69

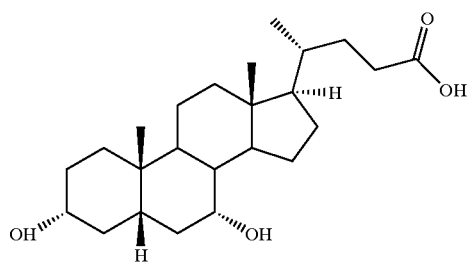

Carboxysteroids
CDCA

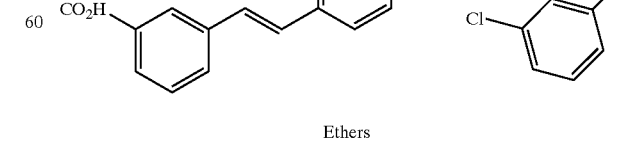

Ethers
GW 4064

Genes found to be regulated by GW 4064 are genes down-regulated in the liver, genes up-regulated in the liver and genes having altered expression in the intestine.

Genes down-regulated in the liver include apolipoprotein B; plasma proteinase inhibitor alpha-1-inhibitor III group 3(m22360); L-glucono-gamma-lactone oxidase (d12754); peroxisomal enoyl-CoA: hydrotase-3-hydroxyacyl-CoA bifunctional enzyme (k03249); liver fatty acid binding protein (L-FABP, m13501), CYP4A2 (m57719), CYP3A23 (x96721) and CYP3A1 (x64401); Cholesterol-7-alpha-hydroxylase, CYP7A1 (RefSeq NM000780, XM 005022, XM 044651, and XM 044652); and sodium-taurocholate cotransport protein, ntcp (RefSeq NM003049, XM007466).

Genes that up-regulate in the liver include small heterodimer partner homolog (d86580); bile salt export pump, bsep (RefSeq NM 003742, XM 003644, and XM 033122); phospholipid transfer protein, PLTP (RefSeq NM 006227, XM 009490, XM 029929, and XM 029930); amithine palmitoyltransferase II, CPTII (RefSeq NM 000098, XM 001758, XM 038866, and XM 038867); phenylethanolamine-N-methyltransferase, PNMT (RefSeq NM 002686, XM 008597, and XM 049837); insulin-induced growth-response protein CL-6 (I13619); elongation factor 2, EF-2 (y07504); mouse cornichon; protein kinase C receptor (u03390); mitochondrial cytochrome C oxidase (m27315); cystathione gamma-lyase (x53460, d17370); cytosolic phosphoenolypyruvate carboxykinase (k03243); histidase (m58308); S-adenosylmethionine synthetase (x60822); lanosterol 14-alpha-demethylase (u17697); G protein-coupled purinoceptor P2U (146865) and hepatic squalene synthetase (m95591).

Genes having altered expression in the intestine include lipase (x61925); pancreatic lipase (d88534); colipase (m58370); pancreatic phospholipase A-2 (d00036); pancreatic amylase (m24962); carboxypeptidase A1 (m23986); carboxypeptidase A2 (m23721): carboxypeptidase B (m23959): pancreatic trypsin I (j00778): pancreatic cationic trypsinogen (m16624); pancreatitrypsinogen II (v01274); elastase I (v01234,I00112); elastase II (I00118, I00124); I-BABP (I22788); intestinal fatty acid binding protein (FABP, k01180); hepatic squalenesynthetase (m95591); protein kinase C receptor (u003390): longation factor 2, EF-2 (y07504) and small heterodimer partner homolog (d86580).

Thus, the invention also concerns a method of modulating a gene whose expression is regulated by the NR1H4 receptor in a mammal comprising administration of a therapeutically effective amount of a compound according to the invention to the mammal.

It is known that the orphan receptor FXR can bind the response element of the SHP gene as a heterodimer with RXR (9-cis retinoic acid receptor) and the SHP-protein, in turn, prevents efficient transcription from the cyp7a1 promoter (Lu et al., Mol Cell, 6(3):505–17; Goodwin et al. Mol Cell, 6(3), 717–26, 2000). Another gene that is repressed via SHP upon FXR activation is the sodium/bile acid cotransporter gene, NTCP, a membrane transport protein which is required for the import of conjugated bile acids in the hepatocyte (Denson et al., Gastroenterology; 121(1): 218–20, 2001). The gene for the bile salt export pump, a membrane transporter responsible for the secretion of bile acids into the gall is directly activated by FXR (Ananthanarayanan et al., J Biol Chem, 3;276(31): 28857–28865, 2001). Consequently, the invention likewise concerns a method for lowering the expression of cholesterol 7-alpha-hydroxylase and NTCP and increasing expression of BSEP in parallel by use of the compounds according to the invention. In one embodiment the invention concerns a method for enhancing the expression of the Intestinal Bile Acid Binding Protein (1-BABP) (Grober et al., J Biol Chem, 15;274(42):29749–54, 1999 and/or the activity of the canicular bile salt excretion pump.

The compounds according to the invention may be used as medicaments, in particular for the prevention or treatment of a NR1H4 receptor protein- or NR1H4 receptor protein homologue-mediated disease or condition in a mammal wherein the prevention or treatment is directly or indirectly accomplished through the binding of the compound according to the invention to the NR1H4 receptor protein or NR1H4 receptor protein homologue. These pharmaceutical compositions contain 0.1% to 99.5% of the compound according to the invention, more particularly 0.5% to 90% of the compound according to the invention in combination with a pharmaceutically acceptable carrier.

The invention also concerns the use of a compound or combination of compounds according to the invention for the prevention or treatment of a NR1H4 receptor protein-mediated disease or condition wherein the mammal described above is a human. The medicament may be used for regulating the bile transport system in a mammal, preferentially a human, by activating the NR1H4 receptor, for regulating levels of cholesterol, triglyceride, and/or bile acid. For example, the medicament may be used for the treatment of atherosclerosis, gallstone disease, lipid disorders, obesity or a cardiovascular disorder.

The invention further concerns the use of a compound or combination of compounds according to the invention for blocking in a mammal, preferentially a human, fatty acid absorption in the intestine. Further the compounds of the invention may be used for treating obesity in humans and for modulating a gene whose expression is regulated by the NR1H4 receptor (see details above and figures). The invention also further concerns the use of a compound or combination of compounds as antitumor medicaments. The antitumor effects of such medicaments could be exerted by selective inhibition of cell proliferation and induction of apotptosis of tumor cells in a way similar to described activities for certain bisphosphonates (Alberts D S, et al., Clin Cancer Res 2001 May; 7(5):1246–50).

The following examples illustrate a specific embodiment of the invention, but they are not to be considered as limiting the invention in any manner.

EXAMPLE 1

For in vitro screening for compounds which influence FXR binding to coactivators, a fragment of the open reading frame of human FXR alpha (NR1H4-(Acc. No:AF384555)) encoding aminoacids 187–472 was amplified by standard RT PCR procedures (see SEQ ID NOS. 1 and 2 in FIGS. 4A and 4B, respectively). The starting material was total RNA derived from human liver. The resulting cDNA obtained after reverse transcription was subsequently cloned using the Gateway™ recombination technology (Invitrogen, USA) into the expression plasmid pDest15 (Invitrogen, USA). This construct was used to express a recombinant GST-FXR fusion protein in *E. coli* (BL21 strain). A pDEST 17 derivative clone harboring an additional sequence encoding amino acids 548–878 of human TIF2 (Acc. No: XM_011633 RefSeq) was constructed using Gateway™ recombination technology (Invitrogen, USA) in order to obtain a construct which was used to express recombinant His-tagged TIF2 fragment in *E. coli*. For *E. coli* expression of both constructs, plasmid DNA was transformed into chemically competent *E. coli* BL21 (Invitrogen, USA) and cells were grown to an OD600 of 0.4–0.7 before expression was induced by addition of 0.5 mM IPTG according instructions of the manufacturer (Invitrogen). After induction for 8 hours at 30° C., the cells were harvested by centrifugation for 10 minutes at 5000×g. Fusion proteins were affinity purified using Glutathion sepharose (Pharmacia) or Ni-NTA Agarose (QIAGEN) according to the instructions of the respective manufacturer. Recombinant proteins were dialyzed against 20 mM Tris/HCL pH 7.9; 60 mM KCl; 5 mM $MgCl_2$; 1 mM DTT, 0.2 mM PMSF; 10% glycerol. The TIF2 fragment was subsequently biotinylated by addition of 40–120 µl of a biotinamidocaproate N-hydroxysuccinimide-ester (Sigma) solution (20 mg/ml in DMSO). Overhead rotating samples were incubated for 2 hours at room temperature. Unincorporated label was then separated using G25 Gel filtration chromatography (Pharmacia Biotech, Sweden). Protein containing fractions from the column were pooled and tested for activity in the assay as described below.

For screening of the compound libraries as provided for by the methods described in Examples 2, 3 and 4 below for substances which influence the FXR/Tif 2 interaction, Perkin Elmer LANCE technology was used. This technoligy relies on the binding dependent energy transfer from a donor to an acceptor fluorophore attached to the binding partners of interest. For ease of handling and reduction of background from compound fluorescence, LANCE technology makes use of generic fluorophore labels and time resoved detection. For a detailed description of this technoligy, see Hemmilä I, Blomberg K and Hurskainen P, Time-resolved resonance energy transfer (TR-FRET) principle in LANCE, Abstract of Papers Presented at the 3 rd Annual Conference of the Society for Biomolecular Screening, Sep., California (1997).

For screening, 20–200 ng of biotinylated Tif 2 fragment and 10–200 ng of GST-FXR fragment were combined with 0.5–2 nM LANCE Eu-(W1024) labelled anti-GST antibody (Perkin Elmer) and 0.5–2 µg of highly fluorescent APC-labeled streptavidin (Perkin Elmer) in the presence of 50 µM of individual compounds to be screened in a total volume of 25 µl of 20 mM Tris/HCl pH 7.9; 60 mM KCl; 5 mM MgCl2; and 160 ng/µl BSA. DMSO content of the samples was kept below 4%. The samples were incubated for a minimum of 60 minutes in the dark at room temperature in FIA-Plates black 384well med. binding (Greiner).

The LANCE signal was detected by a Perkin Elmer VICTOR2V™ Multilabel Counter applying the detection parameters listed in Table 2 below.

TABLE 2

| | |
|---|---|
| Number of repeats | 1 |
| plate: | GREINER FIA-Plate black 384 well med. binding |
| Measurement height | 3.50 mm |
| Label technology | TR-F Lance |
| Emission filter name | D615 |
| Emission filter slot | A1 |
| Emission aperture | Normal |
| Excitation filter | D340 |
| Delay | 50 µs |
| Window time | 400 µs |
| Cycle | 1000 µs |
| Light integrator capacitors | 1 |
| Light integrator ref. level | 95 |
| Flash energy area | High |
| Flash energy level | 223 |
| Flash absorbance measurement | No |
| Beam | Normal |
| Label technology | TR-F Lance |
| Emission filter name | D665 |

TABLE 2-continued

| | |
|---|---|
| Emission filter slot | A8 |
| Emission aperture | Normal |
| Excitation filter | D340 |
| Delay | 50 µs |
| Window time | 400 µs |
| Cycle | 1000 µs |
| Light integrator capacitors | 1 |
| Light integrator ref. level | 95 |
| Flash energy area | High |
| Flash energy level | 223 |
| Flash absorbance measurement | No |
| Beam | Normal |

The results were visualized by plotting the ratio between the emitted light at 665 nm and at 615 nm. For every batch of recombinant proteins amount of proteins and labeling reagents giving the most sensitive detection of hits were determined individually by analysis of dose response curves for chenodeoxycholic acid.

The methods of preparing 2-aminothiazole derivative compounds and combinatorial libraries are set forth in Examples 2, 3 and 4 below.

EXAMPLE 2

Figures 1, 1A, 2:
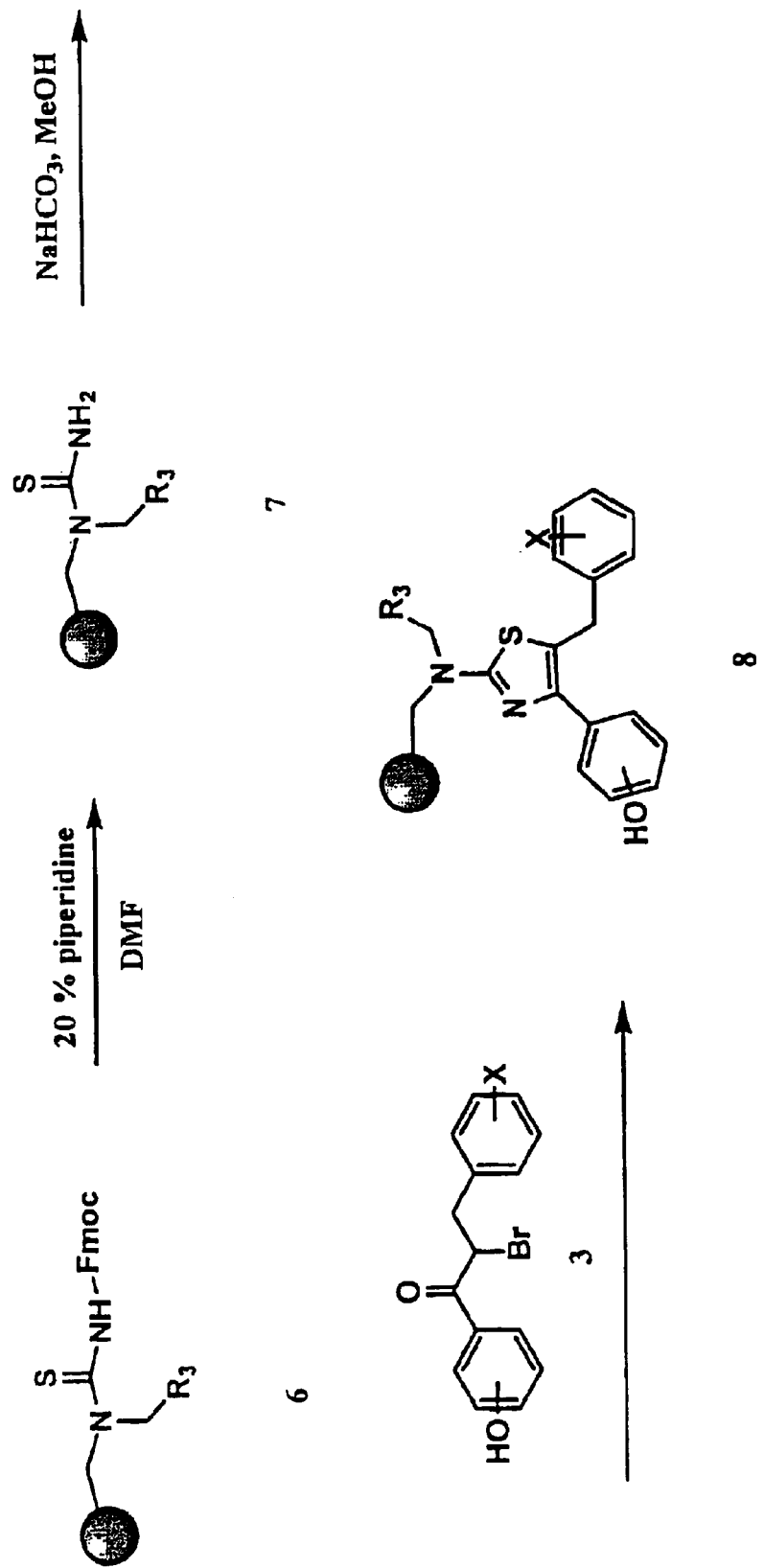
FIG. 2 shows the synthesis of the compounds of the invention described in Example 3.
Figure 1B:
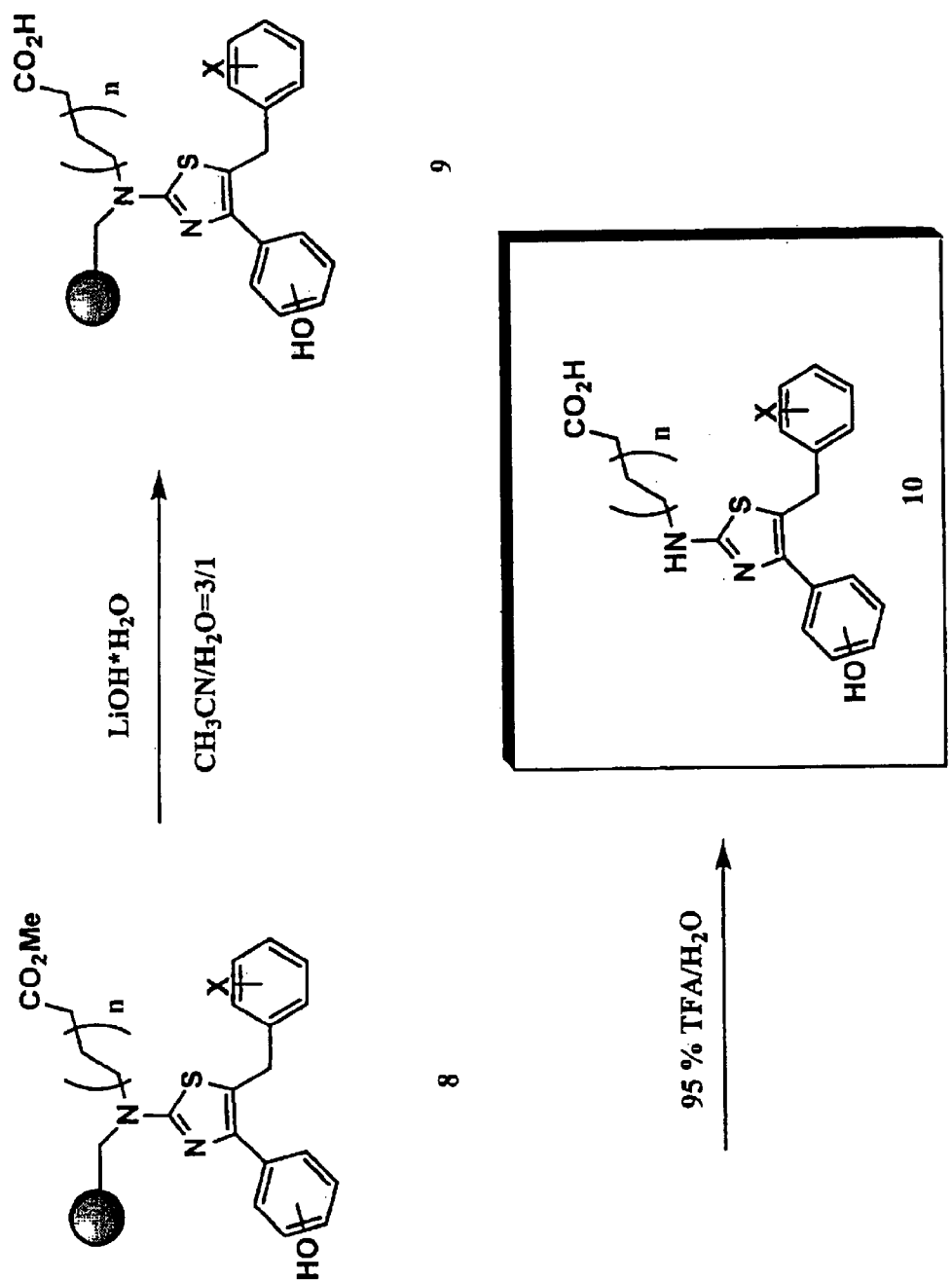

The following steps describe the experimental procedure for the preparation of the compounds according to the invention utilizing ArgoGel-MB-CHO resin. The synthesis scheme is shown in FIGS. 1A and 1B.

Step 1. Synthesis of Chalcone (compound 1)

To a solution of acetophenone (0.05 mol) and aldehyde (0.05 mol) in 150 ml of MeOH was added 2.5 eq of NaOH as pellets. The reaction bottle was placed on a shaker (slightly exothermic reaction) for 24–48 hrs. Then the reaction container was placed in an acetone-ice bath (−5 to 0° C.) and the reaction mixture was quenched with 10.3 ml of 37% aqueous HCl (2.5 eq). Solvent was removed in vacuo and the residue was partitioned between EtOAc and water. The aqueous layer was discarded and the organic layer was washed with water, brine and dried over $Na_2SO_4$. Solvent was removed in vacuo and the crude chalcone (compound 1) was recrystallized from methanol (MeOH) or a mixture of hexane and ethyl acetate (Hex:EtOAc) 3:1 or purified by silica gel chromatography using a mixture of Hex:EtOAc= 5:1 as an eluent.

Step 2. Preparation of 1,3-Diphenylpropan-1-one (compound 2)

Chalcone (compound 1) (37.6 mmol) was dissolved in 250 ml of toluene (in some cases 25 ml of MeOH was added to insure a complete dissolution) and 400 mg of 10% Pd/C (0.01 eq) was added to the mixture. The compound was hydrogenated at 45 psi in a Parr apparatus for 40 min to 3 hrs to form 1,3-diphenylpropan-1-one (compound 2), during which time the reaction mixture was periodically checked for the starting material by TLC (Hex:EtOAc=1:1) to prevent over-reduction. Upon completion of reduction the reaction mixture was filtered through a short pad (2–3 inch) of silica gel and solvent was removed in vacuo to afford a crude product, which was either sufficiently pure to use in the next step or was purified by recrystallization from MeOH or Hex:EtOAc=3:1 or, in the case where over-reduction has occurred, by silica gel column chromatography using Hex:EtOAc=5:1 as an eluent.

Step 3. Preparation of 2-Bromo-1,3-Diphenylpropan-1-one (compound 3)

To a solution of 1,3-diphenylpropan-1-one (compound 2) (7.0 mmol) in 25 ml of anhydrous dioxane, a solution of bromine (7.0 mmol) in 10 ml of dioxane was slowly added dropwise over 30 min. The reaction mixture was left to stir at room temperature for 24 hrs to form 2-bromo-1,3-diphenylpropan-1-one (compound 3). Solvent was removed in vacuo. The 2-bromo-1,3-diphenylpropan-1-one product formed was determined by $^1$H NMR to be sufficiently pure to be used in the next step.

Step 4. Reductive Amination of Argogel-MB-CHO Resin (4) with Primary Amines to form Aminated Argogel-MB-HCO resin (5)

Argogel-MB-CHO resin (Argonaut Technologies Inc.) (100 mg each tea-bag [Houghten, U.S. Pat. No. 4,631,211], 0.41 mmol/g substitution) (compound 4) was swollen in 1% acetic acid (AcOH) in DMF (by volume). The amine (10 eq.) was added and the bottle(s) placed on a shaker for 30 min. Solid NaBH$_3$CN (20 eq) was added and the reaction bottle(s) placed on a shaker at room temperature for 18 hrs to form resin aminated Argogel-MB-HCO resin (5). The resin was washed as follows: DMF (4×), MeOH (4×), CH$_2$Cl$_2$ (2×) and then allowed to air dry. For the amines that were hydrochloride salts, 1 eq of Et$_3$N was added.

Step 5. Preparation of a resin-bound thiourea (compound 7)

A 0.2 M solution of Fmoc-NCS (5 eq) in anhydrous CH$_2$Cl$_2$ was added to a bottle containing the aminated Argogel-MB-HCO resin (resin compound 5). The bottle was placed on a shaker for one hour to form resin compound 6. The resin was washed with CH$_2$Cl$_2$ (3×) and DMF (3×) and subsequently reacted with 20% piperidine in DMF (5 eq) for one hour to produce a resin-bound thiourea (resin compound 7). The resin was then washed with DMF (3×) and MeOH (3×) and used directly in the next step.

Step 6. Preparation of the resin-bound 2-aminothiazole (compound 8)

The resin was placed a reaction bottle and the resin was swollen in MeOH and NaHCO$_3$ (10 eq) was added to the solution. The reaction bottle was placed on a shaker for 10 min, then a 0.2 M solution of 2-bromo-1,3-diphenylpropan-1-one (15 eq) (compound 3) in MeOH was added to the mixture and the bottle was placed on a shaker for 24 hrs to form resin-bound 2-aminothiazole. Then the solution mixture was decanted and the resin was washed with MeOH (4×), CH$_3$CN/H$_2$O=1/1 (3×), CH$_3$CN (2×) and was taken directly to the next step.

Step 7. Hydrolysis of the ester 8 to the acid (compound 9)

Tea-bags were placed in a bottle containing 0.5 M solution of LiOH*H$_2$O (100 eq) in a mixture CH$_3$CN/H$_2$O=3/1. For the purpose of this example, R$_3$ in compound 8 in FIG. 1B is —(CH$_2$—CH$_2$)$_n$—CH$_2$—CO$_2$CH$_3$ where n is an integer from 0 to 8, preferably 1 to 6 and more preferably 1 to 4. The bottle was placed on a shaker for 24 hrs. Then bags were washed with CH$_3$CN/H$_2$O=3/1 (3×), H$_2$O (2×), then briefly treated with 1N HCl (1 min, 1×), then washed with water (3×), CH$_3$CN/H$_2$O=3/1 (3×), CH$_3$CN (2×), CH$_2$Cl$_2$ (2×) and air-dried to form acid compound 9.

Step 8. Cleavage of 2-aminothiazole (compound 10) from resin

Tea-bags (100 mg of resin each) were placed in vials and 3 ml of 95% aqueous TFA were added to each vial. The vials were tightly capped and placed in an oven-shaker at 50° C. for 3 hrs. The eluate was collected, combined with one subsequent TFA wash and the solvent was removed with a Genevac. The crude material was analyzed by LCMS (Thermo Finnigan LCQ-classic) and if necessary purified by HPLC. The product from was a 2-aminothiazole (compound 10).

EXAMPLE 3

Experimental procedure for the preparation of the compounds according to the invention utilizing Wang resin. The synthesis scheme is shown in FIG. 2.

Step 1. Immobilization of a carboxylic acid (compound 11) on Bromo-Wang resin Bromo-Wang resin (100 mg each tea-bag, 1.00 mmol/g substition) was swollen in anhydrous DMF. A carboxylic acid (compound 11) (5 eq.) was added, followed by potassium iodide (5 eq) and cesium carbonate (5 eq), and the bottle(s) placed in an oven-shaker at 80° C. for 3 days. Then the reaction mixture was decanted and the resin was washed as follows: DMF (4×), MeOH (4×), CH$_2$Cl$_2$ (2×) and then allowed to air dry to form resin compound 12.

Step 2. Preparation of the resin-bound thioureas (compound 15)

Resin compound 12 was placed in a bottle and the resin compound was swollen in 20% piperidine in DMF (5 eq). Tea-bags were placed in the bottle and the bottle was placed on a shaker at room temperature for one hour. Then the resin was washed with DMF (3×), MeOH (3×), CH$_2$Cl$_2$ (3×) to form resin compound 13. Then a 0.1 M solution of Fmoc-NCS (5 eq) in anhydrous CH$_2$Cl$_2$ was applied to resin compound 13 in the bottle and the bottle was placed on a shaker for one hour. The resin was then washed with CH$_2$Cl$_2$ (3×) and DMF (3×) and subsequently reacted again with 20% piperidine in DMF (5 eq) for one hour to produce the resin-bound thiourea (compound 15). The resin was then washed with DMF (3×) and MeOH (3×) and used directly in the next step.

Step 3. Preparation of a Resin-Bound 2-Aminothiazole (compound 16)

The resin-bound thiourea was placed in a reaction bottle and the resin was swollen in MeOH and NaHCO$_3$ (5 eq) was added to the solution. The reaction bottle was placed on a shaker for 10 min, then a 0.1 M solution of 2-bromo-1,3-diphenylpropan-1-one (compound 3) (5 eq) in MeOH was added to the mixture and the bottle was placed on a shaker for 2 days. Then the solution mixture was decanted and the resin was washed with MeOH (4×), CH$_3$CN/H$_2$O=1/1 (3×), CH$_3$CN (2×), CH$_2$Cl$_2$ (2×) and air-dried to form resin-bound 2-aminothiazole (compound 16).

Step 4. Cleavage of 2-aminothiazole to form products 10 from resin.

Tea-bags (100 mg of resin each) were placed in vials and 3 ml of 50% TFA in CH$_2$Cl$_2$ were added to each vial. The vials were tightly capped and placed on a shaker at room temperature for 3 hrs. The eluate was collected and combined with one subsequent TFA wash. Then the solvent was removed with a Genevac. The crude material was analyzed by LCMS (Thermo Finnigan LCQ-classic), and if necessary purified by HPLC-MS, to form product 10.

EXAMPLE 4

Figure 3:
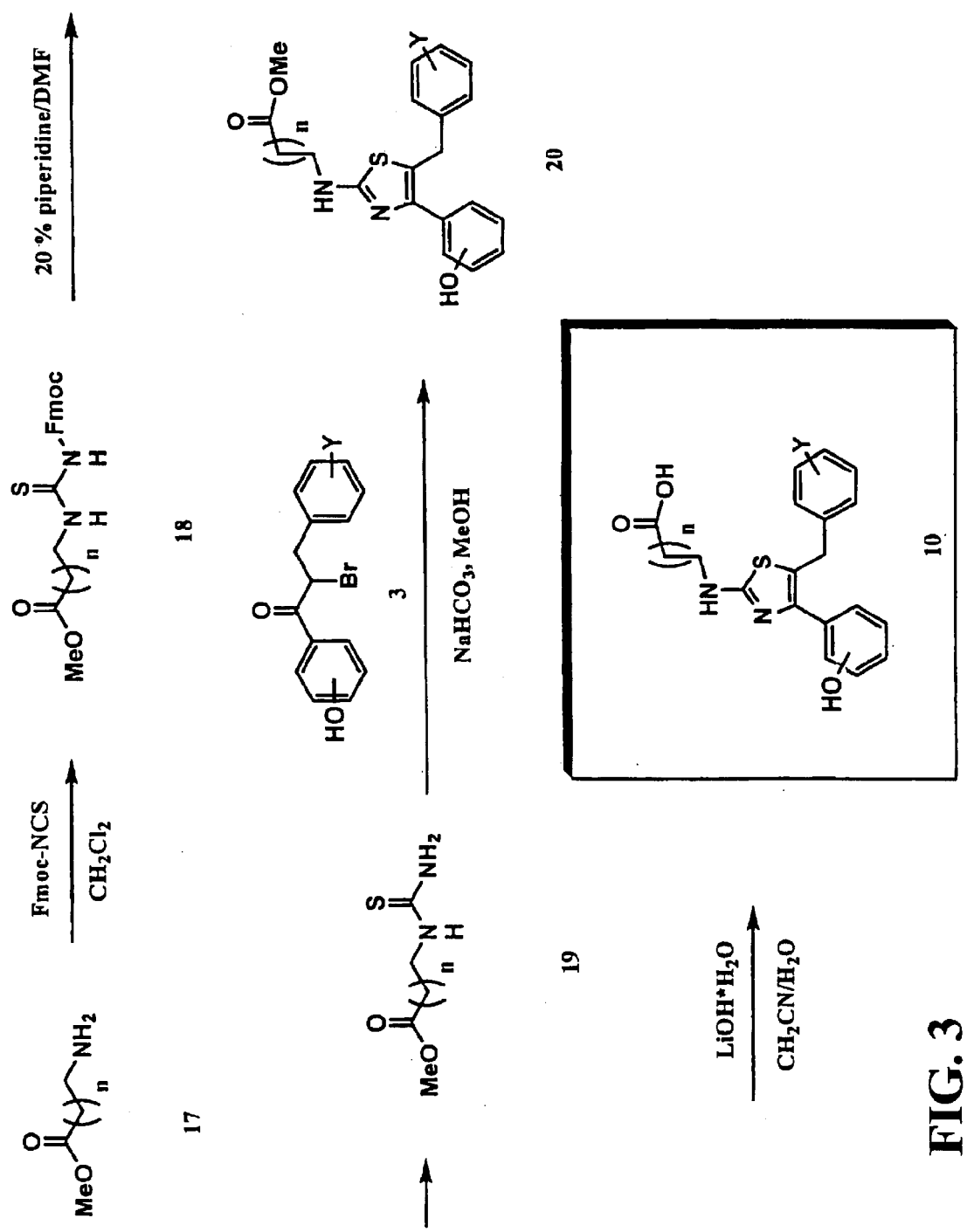
FIG. 3 shows the synthesis of the compounds of the invention described in Example 4.

Experimental procedure for the preparation of the compounds according to the invention utilizing solution-phase chemistry is shown in FIG. 3.

Step 1. Preparation of a Fmoc-Protected Thiourea (compound 18)

To a solution of an HCl salt of amine compound 17 (25 mmol) in 200 ml of anhydrous $CH_2Cl_2$, $Et_3N$ (25 mmol) was added which was followed by Fmoc-NCS (25 mmol). The reaction mixture was stirred at room temperature for 2 hrs. Then solvent was removed in vacuo to give a crude bright-yellow solid Fmoc-protected thiorurea product (compound 18) in a quatitative yield.

Step 2. Fmoc-deprotection of Thiourea Compound 18

The crude product (compound 18) from the previous step (25 mmol) was dissolved in 20 ml of DMF and 1 ml of piperidine was added. Evolution of gas ($CO_2$) was observed within 5 min and the reaction was slightly exothermic. The reaction mixture was left to stir at room temperature overnight. Then 300 ml of $H_2O$ were added and the mixture was extracted extensively with EtOAC (150 ml, 5×). The combined extracts were dried over $Na_2SO_4$, solvent was removed in vacuo to give a yellow solid Fmoc-deprotected thiourea compound 19, to which 50 ml of $CH_2Cl_2$ were added and the suspension was filtered. The precipitate, compound 19, was collected on a filter, washed with a small amount of $CH_2Cl_2$ and dried in vacuo.

Step 3. Formation of a 2-aminothiazole (compound 20)

To a solution comprising 2-bromo-1,3-diphenylpropan-1-one (compound 3) (1.0 mmol) and Fmoc-deprotected thiourea (compound 19) (1.0 mmol) in 15 ml of MeOH, $NaHCO_3$ (1.0 mmol) was added and the reaction mixture was heated at 50° C. for 24 hours. Then solvent was removed in vacuo, and the residue was partitioned between EtOAc and water to form 2-aminothiazole (compound 20) which was washed with brine, dried over $Na_2SO_4$. Solvent was removed in vacuo and the residue was purified by silica gel chromatography using Hex:EtOAc=3:1 as eluent.

Step 4. Hydrolysis of Ester Compound 20 to Acid Product 10

To a solution of the 2-aminothiazole compound 20 (2.0 mmol) in 9 ml of $CH_3CN$, a solution of $LiOH*H_2O$ in 3 ml of $H_2O$ was added. The mixture was stirred at room temperature for 24 hours, then it was acidified to pH 3 by 1 N HCl and extracted with EtOAc (3×). The extracted product was washed with brine, dried over $Na_2SO_4$ and solvent was removed in vacuo to give the product 10 as a light-yellow solid, which was purified by HPLC.

Tables 3, 4, 5 and 6 illustrate the preferred compounds according to the invention that can mediate transactivation of FXR mediated transcription in a HEK293 reporter cell line. The data summarized in the Tables below which shows the internal molecular name used by Applicant (MOLNAME) as well as the corresponding structures of preferred compounds accoring to the invention. The Table provides the $EC_{50}$ values (EC50 AGV) as established as well as their respective average efficacy (% activity relative to CDCA control agonist).

TABLE 3

| MOLNAME | MOLECULAR STRUCTURE | EC50 AVG | EFFIC AVG | EXPECTED MASS | FOUND MASS |
|---|---|---|---|---|---|
| LN0000006316 | 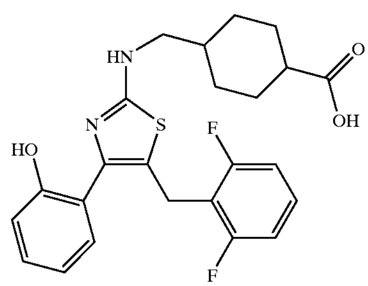 | 0.20 | 110 | 458.53 | 459.28 |
| LN0000006322 | 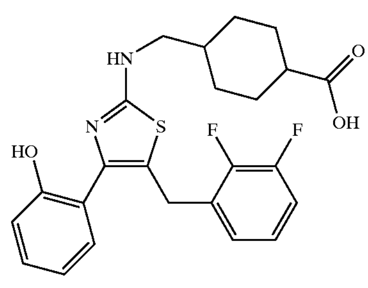 | 1.45 | 115 | 459.53 | 459.29 |

TABLE 3-continued

| MOLNAME | MOLECULAR STRUCTURE | EC50 AVG | EFFIC AVG | EXPECTED MASS | FOUND MASS |
|---|---|---|---|---|---|
| LN0000006323 | 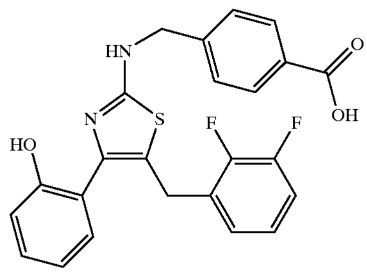 | 0.44 | 86 | 452.48 | 453.22 |
| LN0000006365 | 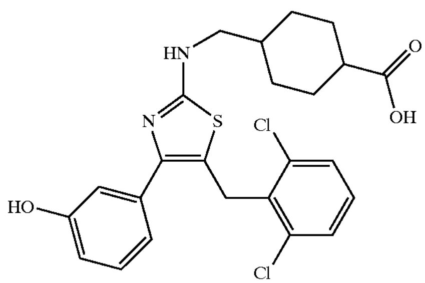 | 0.36 | 92 | 491.44 | 492.21 |

TABLE 4

| MOLNAME | MOLECULE STRUCTURE | EC50 AVG | EFFIC AVG | EXPECTED MASS | FOUND MASS |
|---|---|---|---|---|---|
| LN0000006317 | | 1.45 | 115 | 452.48 | 453.22 |
| LN0000006328 | | 4.50 | 116 | 452.58 | 459.26 |
| LN0000006329 | | 0.73 | 105 | 446.53 | 447.23 |

TABLE 4-continued

| MOLNAME | MOLECULE STRUCTURE | EC50 AVG | EFFIC AVG | EXPECTED MASS | FOUND MASS |
|---|---|---|---|---|---|
| LN0000006339 | | 2.32 | 86 | 458.43 | 459.28 |

TABLE 5

| MOLNAME | MOLECULAR STRUCTURE | EC50 AVG | EFFIC AVG | EXPECTED MASS | FOUND MASS |
|---|---|---|---|---|---|
| LN0000006346 | 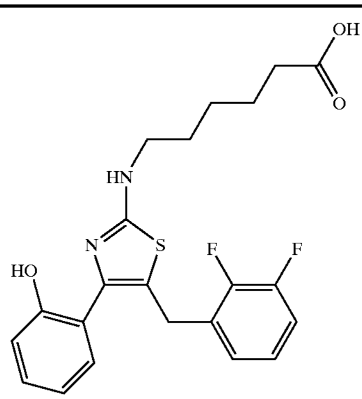 | 5.12 | 63 | 432.49 | 433.25 |
| LN0000006347 | 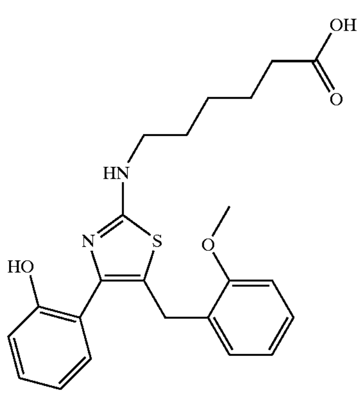 | 3.10 | 66 | 426.54 | 427.26 |
| LN0000006348 | 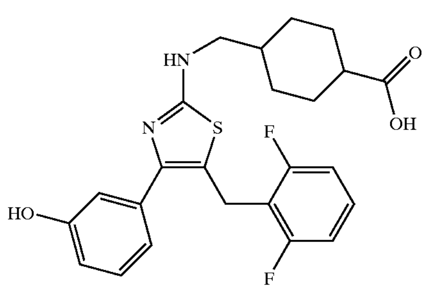 | 2.39 | 109 | 458.53 | 459.29 |

TABLE 5-continued

| MOLNAME | MOLECULAR STRUCTURE | EC50 AVG | EFFIC AVG | EXPECTED MASS | FOUND MASS |
|---|---|---|---|---|---|
| LN0000006349 | 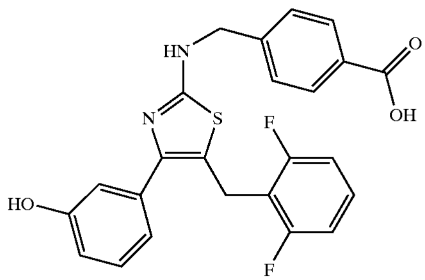 | 4.05 | 66 | 452.48 | 453.22 |

TABLE 6

| MOLNAME | MOLECULAR STRUCTURE | ED50 AVG | EFFIC AVG |
|---|---|---|---|
| LN0000006316 | 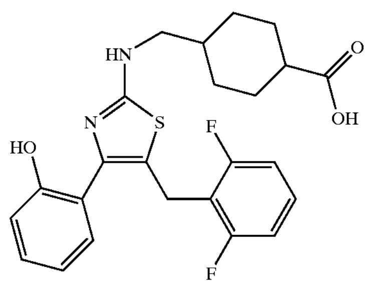 | 12 | 309 |
| LN0000006317 | 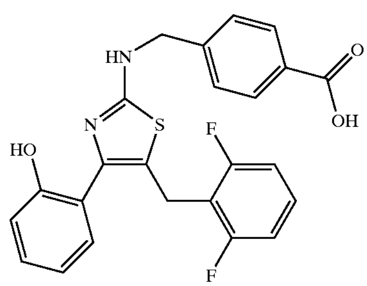 | 15 | 223 |
| LN0000006339 | 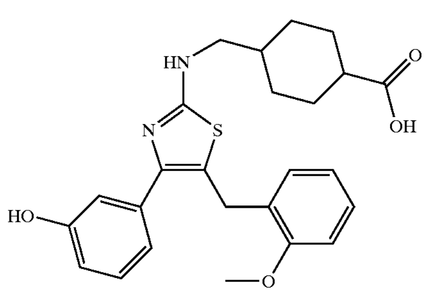 | 20 | 323 |

TABLE 6-continued

| MOLNAME | MOLECULAR STRUCTURE | ED50 AVG | EFFIC AVG |
|---|---|---|---|
| LN0000006365 | 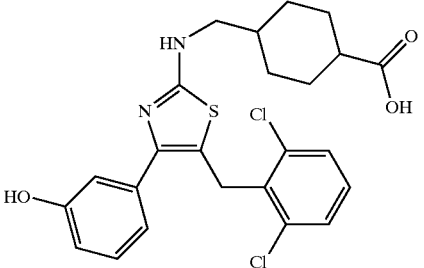 | 15 | 340 |

Stable HEK293FXR reporter cell lines were generated by stably transfecting with the pTRexDest30 (Invitrogen) derivatives pTRexDest30-hFXR, pTRexDest30-hRXR and the pGL2promoter (Promega) derivative pGL2promoter-FXRRE. The full length human FXR (accession U68233) and the full length human RXRα (accession P19793) were cloned into the pTRexDest30 applying the manufacturer protocols for the Gateway™ system (Invitrogen).

The FXR response elements were cloned (upper case and undrelined).
5'-cccaGGGTGAaTAACCTcggggctctgtccctccaatccca GGGTGAaTAACCTcggg 3' (SEQ ID NO. 5) was created from the human IBAB-P promoter (Grober et al 1999, JBC 274, pp. 29749–29754). A stable clone was selected and seeded at a density of 5×10 cells per well in 48 well plates. Luciferase reporter activity was measured in duplicates from extracts of cells after incubating cells in culture medium (DMEM [Gibco-BRL]+10% FCS [PAA laboratories]) for 16 hours (5% $CO_2$, 37° C.) containing 0.5% DMSO (control) or 0.5% DMSO with increasing concentrations of TR0800012996.

While the salient features have been illustrated and described with respect to particular embodiments, it should be readily apparent that modifications can be made within the spirit and scope of the invention, and it is, therefore, not desired to limit the invention to the exact details shown and described.

What is claimed is:

1. A compound including resolved diastereoisomers and enantiomers, and tautomers, pharmaceutical acceptable salts or solvates thereof, having the following formula (I):

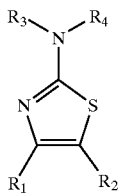

wherein:

$R_1$ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;

$R_2$ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;

$R_3$ is hydrogen;

$R_4$ is selected from the group consisting of $C_1$ to $C_8$ substituted alkyl, wherein the alkyl is substituted with one or more (substituted or unsubstituted) $C_3$ to $C_7$ cycloalkyl, $C_7$ to $C_{12}$ substituted phenylalkyl, wherein the phenyl is substituted with one or more substituents selected from the group consisting of halogen, protected hydroxy, cyano, nitro, $C_2$ to $C_8$ alkyl, $C_1$ to $C_8$ substituted alkyl, $C_1$ to $C_8$ alkoxy, $C_1$ to $C_8$ substituted alkoxy, $C_1$ to $C_8$ acyl, $C_1$ to $C_8$ substituted acyl, to $C_1$ to $C_8$ acyloxy, carboxy, protected carboxy, carboxymethyl, protected carboxymethyl, hydroxymethyl, protected hydroxymethyl, protected amino, (monosubstituted) amino, protected (monosubstitued)amino, (disubstituted)amino, carboxyamide, N,N-di($C_1$ to $C_6$ alkyl)carboxamide, trifluoromethyl, N—(($C_1$ to $C_6$ alkyl)sulfonyl)amino, N-(phenylsulfonyl)amino, cyclic $C_2$ to $C_8$ alkylene and a phenyl group, substituted or unsubstituted and substituted naphthyl.

2. The compound of claim 1, wherein:

$R_1$ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;

$R_2$ is selected from the group consisting of $C_1$ to $C_7$ substituted alkyl, phenyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;

R₃ is hydrogen;
R₄ is:

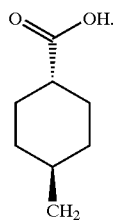

3. The compound of claim 1, wherein:

R₁ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;

R₂ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl and $C_5$ to $C_6$ substituted heteroaryl;

R₃ is hydrogen; and
R₄ is:

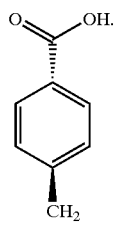

4. The compound according to claim 1, wherein the compound is:

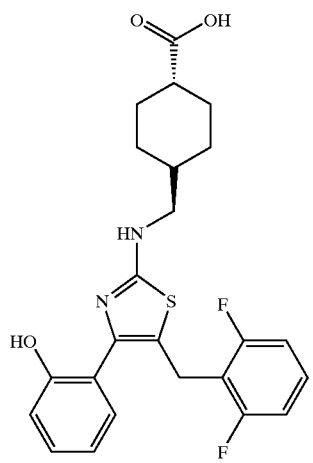

5. The compound according to claim 1, wherein the compound is:

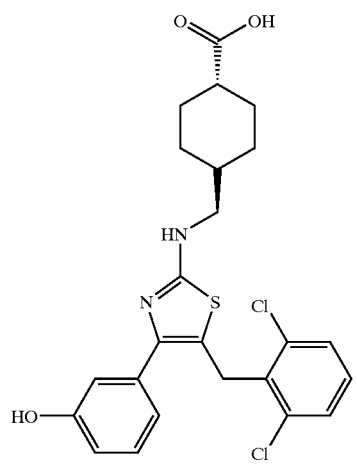

6. The compound according to claim 1, wherein the compound is:

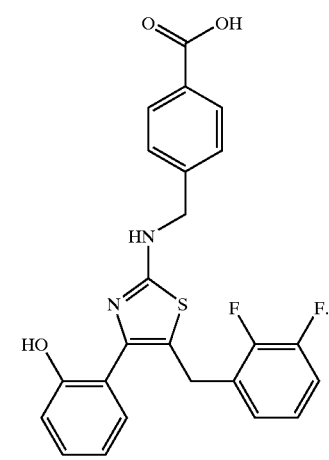

7. The compound according to claim 1, wherein the compound is:

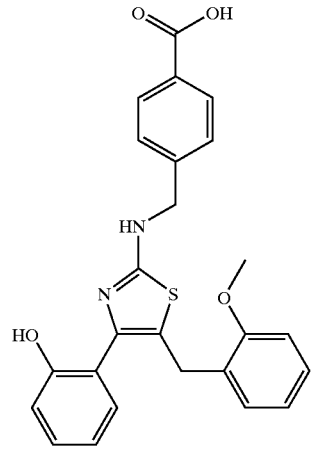

8. The compound according to claim 1, wherein the compound is:

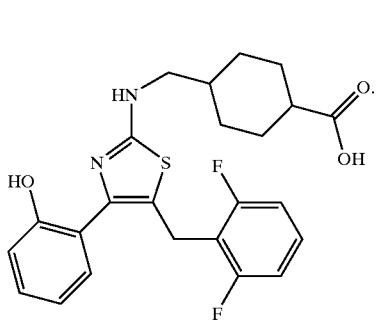

9. The compound according to claim 1, wherein the compound has the following formula:

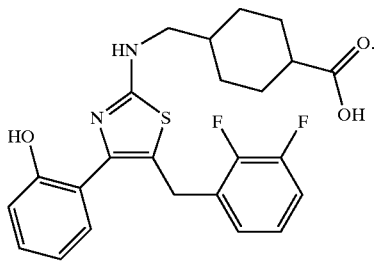

10. The compound according to claim 1, wherein the compound has the following formula:

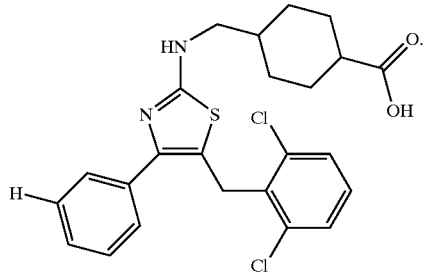

11. The compound according to claim 1, wherein the compound has the following formula:

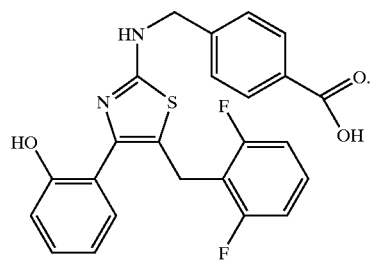

12. The compound according to claim 1, wherein the compound has the following formula:

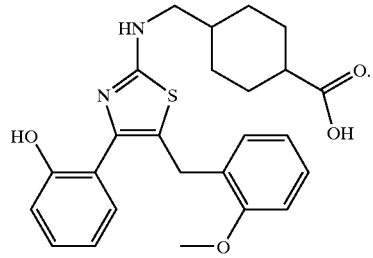

13. The compound according to claim 1, wherein the compound has the following formula:

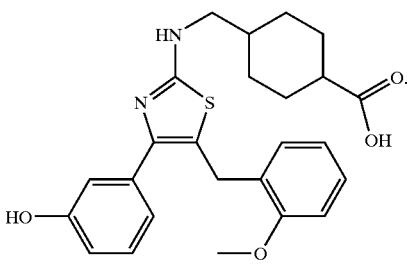

14. The compound according to claim 1, wherein the compound has the following formula:

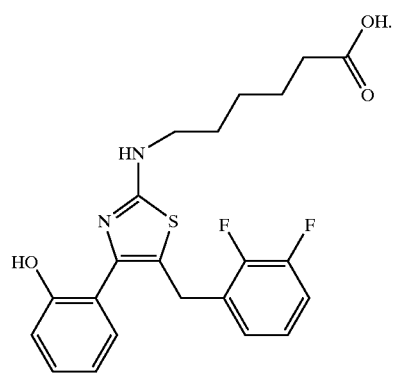

15. The compound according to claim 1, wherein the compound has the following formula:

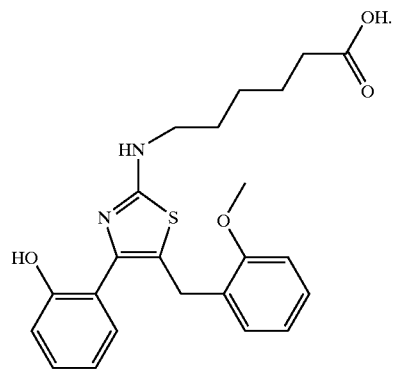

16. The compound according to claim 1, wherein the compound has the following formula:

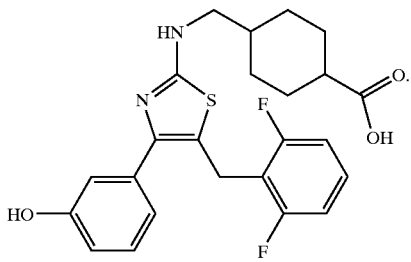

17. The compound according to claim 1, wherein the compound has the following formula:

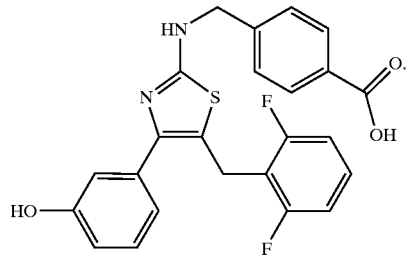

18. A therapeutic composition comprising at least one compound according to any one of claims 1 to 17 in admixture with a pharmaceutically acceptable carrier, adjuvant or vehicle.

19. A compound including resolved diastereoisomers and enantiomers, and tautomers, pharmaceutical acceptable salts or solvates thereof, having the following formula (I):

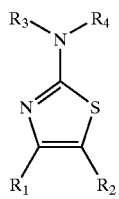

wherein:
  $R_1$ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;
  $R_2$ is selected from the group consisting of $C_1$ to $C_7$ substituted alkyl, substituted phenyl, $C_7$ to $C_{12}$ phenylalkyl, $C_7$ to $C_{12}$ substituted phenylalkyl, $C_2$ to $C_7$ substituted heterocyclic ring, $C_5$ to $C_6$ heteroaryl, and $C_5$ to $C_6$ substituted heteroaryl;
  $R_3$ is hydrogen;
  $R_4$ is selected from the group consisting of the following structures:

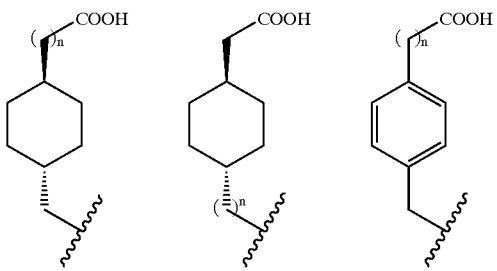

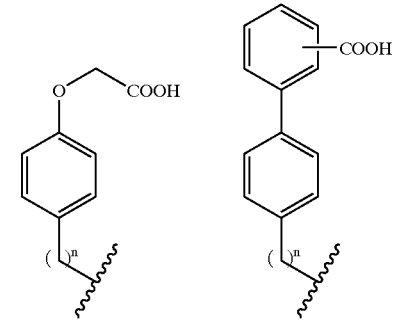

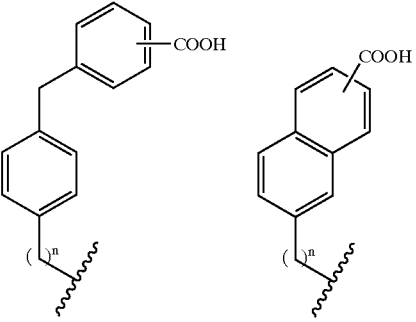

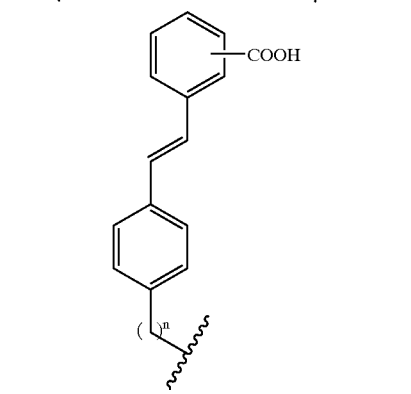

wherein n is an integer from 1 to 3.

* * * * *

UNITED STATES PATENT AND TRADEMARK OFFICE
CERTIFICATE OF CORRECTION

PATENT NO. : 6,974,830 B2  Page 1 of 1
APPLICATION NO. : 10/185731
DATED : December 13, 2005
INVENTOR(S) : Ulrike Bauer et al.

It is certified that error appears in the above-identified patent and that said Letters Patent is hereby corrected as shown below:

Column 2,
Line 27, "Famesoid," should read -- Farnesoid, --.

Figure 2A:
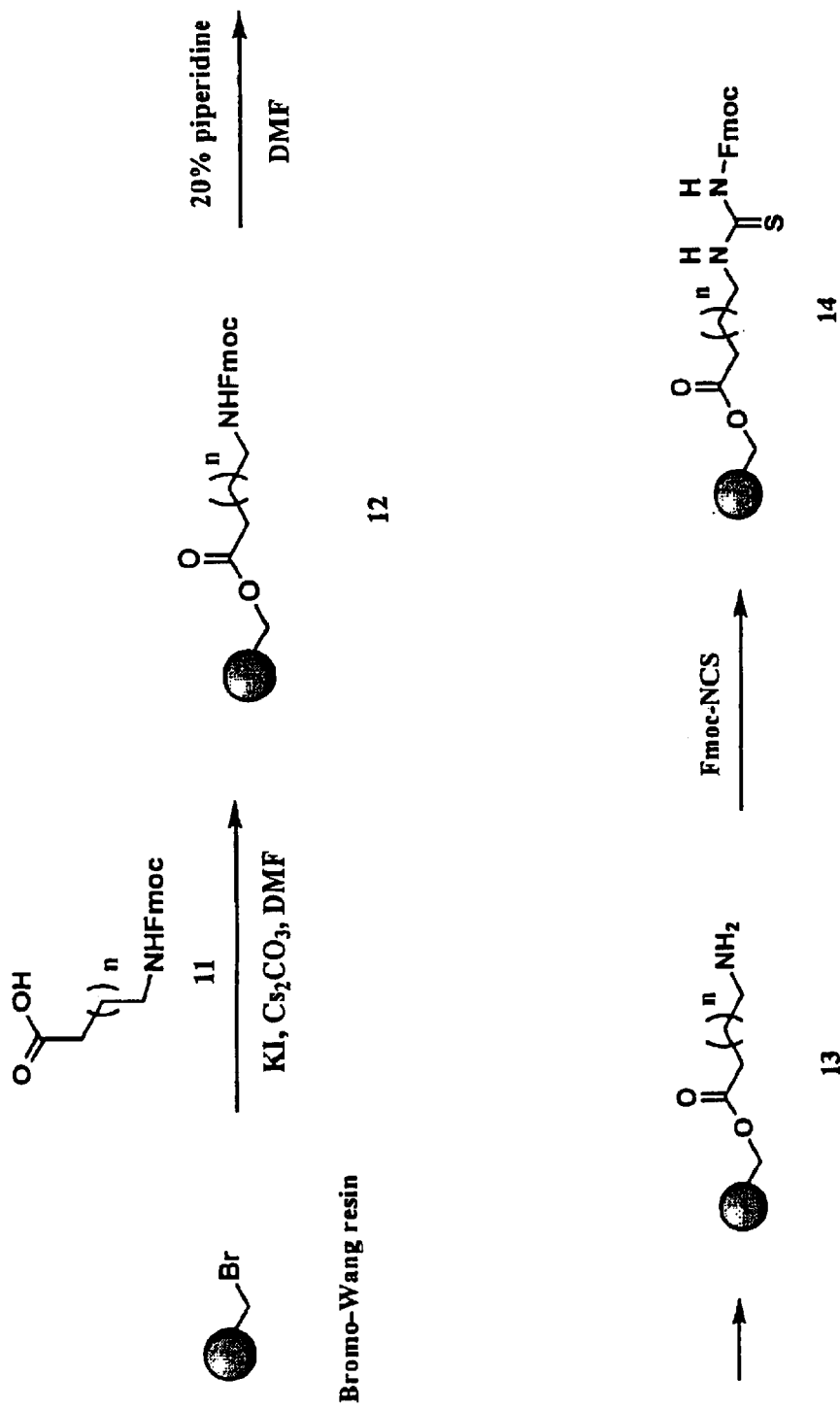
Figure 2B:
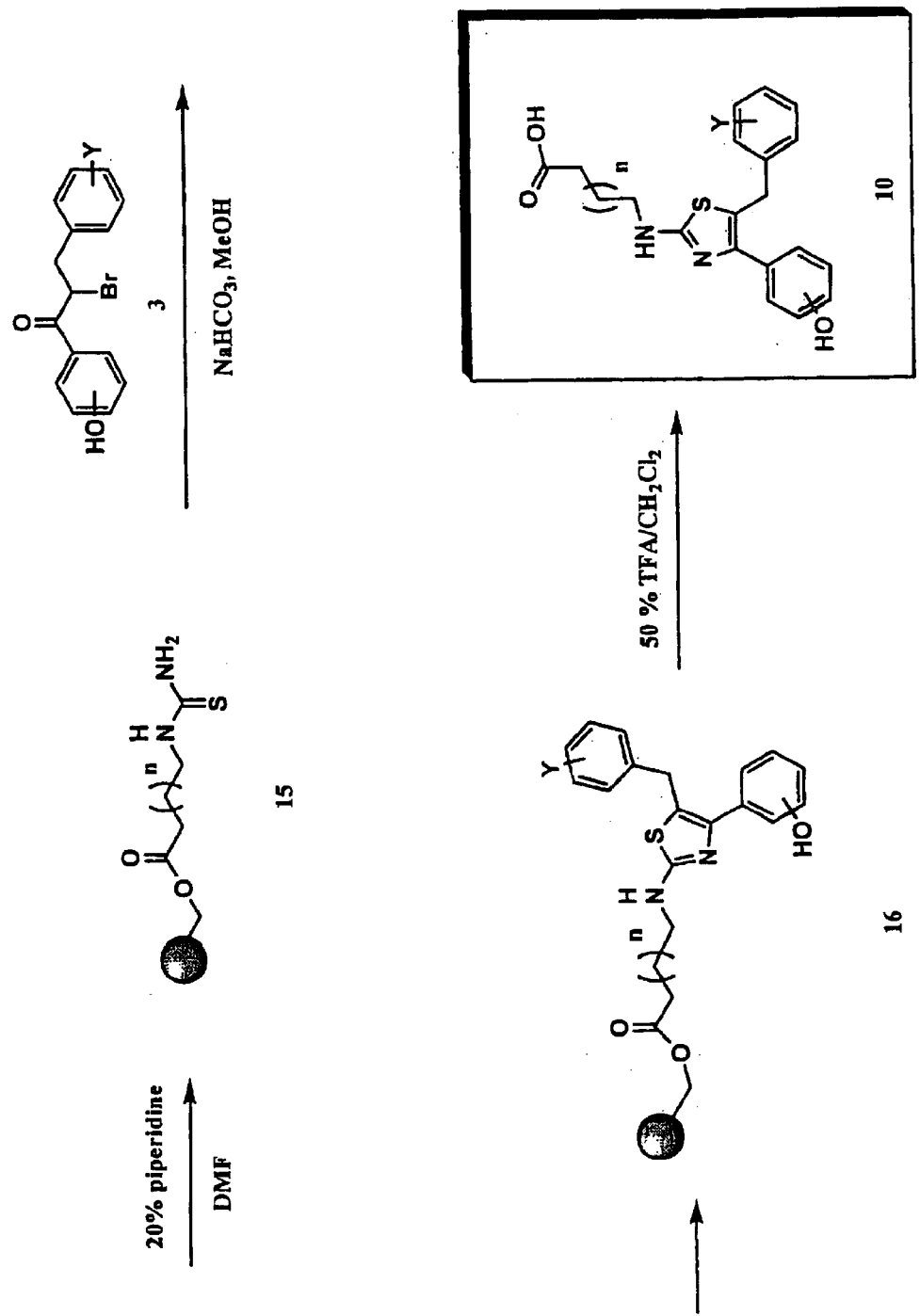

Column 3,
Line 59, "FIGS. 1A and 1B show" should read -- FIGS. 1A-1, 1A-2, and 1B show --.
Line 61, "FIG. 2 shows" should read -- FIGS. 2A and 2B show --.

Column 4,
Line 9, "FIG. 4D shows" should read -- FIGS. 4D-1, 4D-2, 4D-3, 4D-4, and 4D-5
      show --.

Column 13,
Line 1, "following kind aziridine," should read -- following kind: aziridine, --.

Column 17,
Line 38, "pancreatitrypsinogen" should read -- pancreatic trypsinogen --.

Column 18,
Line 18, "(1-BABP)" should read -- (l-BABP) --.

Column 48,
Line 42, Claim 1, "protected hydroxy," should read -- protected hydroxyl, --.
Line 63, Claim 2, "substituted alkyl, phenyl, substituted phenyl," should read
      -- substituted alkyl, substituted phenyl, --.

Signed and Sealed this

Second Day of June, 2009

JOHN DOLL
*Acting Director of the United States Patent and Trademark Office*

SEQUENCE LISTING

<160> NUMBER OF SEQ ID NOS: 5

<210> SEQ ID NO 1
<211> LENGTH: 476
<212> TYPE: PRT
<213> ORGANISM: Homo sapiens

<400> SEQUENCE: 1

```
Met Gly Ser Lys Met Asn Leu Ile Glu His Ser His Leu Pro Thr Thr
 1               5                  10                  15

Asp Glu Phe Ser Phe Ser Glu Asn Leu Phe Gly Val Leu Thr Glu Gln
            20                  25                  30

Val Ala Gly Pro Leu Gly Gln Asn Leu Glu Val Glu Pro Tyr Ser Gln
        35                  40                  45

Tyr Ser Asn Val Gln Phe Pro Gln Val Gln Pro Gln Ile Ser Ser Ser
    50                  55                  60

Ser Tyr Tyr Ser Asn Leu Gly Phe Tyr Pro Gln Gln Pro Glu Glu Trp
65                  70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
    130                 135                 140
```

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Met Tyr Thr Gly Leu Leu Thr Glu Ile Gln Cys Lys
        195                 200                 205

Ser Lys Arg Leu Arg Lys Asn Val Lys Gln His Ala Asp Gln Thr Val
210                 215                 220

Asn Glu Asp Ser Glu Gly Arg Asp Leu Arg Gln Val Thr Ser Thr Thr
225                 230                 235                 240

Lys Ser Cys Arg Glu Lys Thr Glu Leu Thr Pro Asp Gln Gln Thr Leu
                245                 250                 255

Leu His Phe Ile Met Asp Ser Tyr Asn Lys Gln Arg Met Pro Gln Glu
            260                 265                 270

Ile Thr Asn Lys Ile Leu Lys Glu Glu Phe Ser Ala Glu Glu Asn Phe
        275                 280                 285

Leu Ile Leu Thr Glu Met Ala Thr Asn His Val Gln Val Leu Val Glu
290                 295                 300

Phe Thr Lys Lys Leu Pro Gly Phe Gln Thr Leu Asp His Glu Asp Gln
305                 310                 315                 320

Ile Ala Leu Leu Lys Gly Ser Ala Val Glu Ala Met Phe Leu Arg Ser
                325                 330                 335

Ala Glu Ile Phe Asn Lys Lys Leu Pro Ser Gly His Ser Asp Leu Leu
            340                 345                 350

Glu Glu Arg Ile Arg Asn Ser Gly Ile Ser Asp Glu Tyr Ile Thr Pro
        355                 360                 365

Met Phe Ser Phe Tyr Lys Ser Ile Gly Glu Leu Lys Met Thr Gln Glu
370                 375                 380

Glu Tyr Ala Leu Leu Thr Ala Ile Val Ile Leu Ser Pro Asp Arg Gln
385                 390                 395                 400

Tyr Ile Lys Asp Arg Glu Ala Val Glu Lys Leu Gln Glu Pro Leu Leu
                405                 410                 415

Asp Val Leu Gln Lys Leu Cys Lys Ile His Gln Pro Glu Asn Pro Gln
            420                 425                 430

His Phe Ala Cys Leu Leu Gly Arg Leu Thr Glu Leu Arg Thr Phe Asn
        435                 440                 445

His His His Ala Glu Met Leu Met Ser Trp Arg Val Asn Asp His Lys
450                 455                 460

Phe Thr Pro Leu Leu Cys Glu Ile Trp Asp Val Gln
465                 470                 475

<210> SEQ ID NO 2
<211> LENGTH: 1431
<212> TYPE: DNA
<213> ORGANISM: Homo sapiens

<400> SEQUENCE: 2
atgggatcaa aaatgaatct cattgaacat tcccatttac ctaccacaga tgaattttct      60
ttttctgaaa atttatttgg tgttttaaca gaacaagtgg caggtcctct gggacagaac     120
ctggaagtgg aaccatactc gcaatacagc aatgttcagt ttccccaagt tcaaccacag     180
atttcctcgt catcctatta ttccaacctg ggtttctacc cccagcagcc tgaagagtgg     240

-continued

| | |
|---|---|
| tactctcctg gaatatatga actcaggcgt atgccagctg agactctcta ccagggagaa | 300 |
| actgaggtag cagagatgcc tgtaacaaag aagccccgca tgggcgcgtc agcagggagg | 360 |
| atcaaagggg atgagctgtg tgttgtttgt ggagacagag cctctggata ccactataat | 420 |
| gcactgacct gtgagggtg taaaggtttc ttcaggagaa gcattaccaa aaacgctgtg | 480 |
| tacaagtgta aaacggggg caactgtgtg atggatatgt acatgcgaag aaagtgtcaa | 540 |
| gagtgtcgac taaggaaatg caaagagatg ggaatgttgg ctgaatgtat gtatacaggc | 600 |
| ttgttaactg aaattcagtg taaatctaag cgactgagaa aaatgtgaa gcagcatgca | 660 |
| gatcagaccg tgaatgaaga cagtgaaggt cgtgacttgc acaagtgac ctcgacaaca | 720 |
| aagtcatgca gggagaaaac tgaactcacc ccagatcaac agactcttct acattttatt | 780 |
| atggattcat ataacaaaca gaggatgcct caggaaataa caaataaaat tttaaaagaa | 840 |
| gaattcagtg cagaagaaaa ttttctcatt ttgacggaaa tggcaaccaa tcatgtacag | 900 |
| gttcttgtag aattcacaaa aaagctacca ggatttcaga ctttggacca tgaagaccag | 960 |
| attgctttgc tgaaagggtc tgcggttgaa gctatgttcc ttcgttcagc tgagattttc | 1020 |
| aataagaaac ttccgtctgg gcattctgac ctattggaag aaagaattcg aaatagtggt | 1080 |
| atctctgatg aatatataac acctatgttt agttttata aaagtattgg ggaactgaaa | 1140 |
| atgactcaag aggagtatgc tctgcttaca gcaattgtta tcctgtctcc agatagacaa | 1200 |
| tacataaagg atagagaggc agtagagaag cttcaggagc cacttcttga tgtgctacaa | 1260 |
| aagttgtgta agattcacca gcctgaaaat cctcaacact ttgcctgtct cctgggtcgc | 1320 |
| ctgactgaat tacggacatt caatcatcac cacgctgaga tgctgatgtc atggagagta | 1380 |
| aacgaccaca gtttacccc acttctctgt gaaatctggg acgtgcagtg a | 1431 |

<210> SEQ ID NO 3
<211> LENGTH: 1263
<212> TYPE: PRT
<213> ORGANISM: Homo sapiens

<400> SEQUENCE: 3

Met Leu Val Lys Pro Leu Pro Asp Ser Glu Glu Gly His Asp Asn
1               5                   10                  15

Gln Glu Ala His Gln Lys Tyr Glu Thr Met Gln Cys Phe Ala Val Ser
            20                  25                  30

Gln Pro Lys Ser Ile Lys Glu Glu Gly Glu Asp Leu Gln Ser Cys Leu
        35                  40                  45

Ile Cys Val Ala Arg Arg Val Pro Met Lys Glu Arg Pro Val Leu Pro
    50                  55                  60

Ser Ser Glu Ser Phe Thr Thr Arg Gln Asp Leu Gln Gly Lys Ile Thr
65                  70                  75                  80

Ser Leu Asp Thr Ser Thr Met Arg Ala Ala Met Lys Pro Gly Trp Glu
                85                  90                  95

Asp Leu Val Arg Arg Cys Ile Gln Lys Phe His Ala Gln His Glu Gly
            100                 105                 110

Glu Ser Val Ser Tyr Ala Lys Arg His His Glu Val Leu Arg Gln
        115                 120                 125

Gly Leu Ala Phe Ser Gln Ile Tyr Arg Phe Ser Leu Ser Asp Gly Thr
    130                 135                 140

Leu Val Ala Ala Gln Thr Lys Ser Lys Leu Ile Arg Ser Gln Thr Thr
145                 150                 155                 160

```
Asn Glu Pro Gln Leu Val Ile Ser Leu His Met Leu His Arg Glu Gln
            165                 170                 175
Asn Val Cys Val Met Asn Pro Asp Leu Thr Gly Gln Thr Met Gly Lys
            180                 185                 190
Pro Leu Asn Pro Ile Ser Ser Asn Ser Pro Ala His Gln Ala Leu Cys
            195                 200                 205
Ser Gly Asn Pro Gly Gln Asp Met Thr Leu Ser Ser Asn Ile Asn Phe
            210                 215                 220
Pro Ile Asn Gly Pro Lys Glu Gln Met Gly Met Pro Met Gly Arg Phe
225                 230                 235                 240
Gly Gly Ser Gly Gly Met Asn His Val Ser Gly Met Gln Ala Thr Thr
                245                 250                 255
Pro Gln Gly Ser Asn Tyr Ala Leu Lys Met Asn Ser Pro Ser Gln Ser
            260                 265                 270
Ser Pro Gly Met Asn Pro Gly Gln Pro Thr Ser Met Leu Ser Pro Arg
            275                 280                 285
His Arg Met Ser Pro Gly Val Ala Gly Ser Pro Arg Ile Pro Pro Ser
            290                 295                 300
Gln Phe Ser Pro Ala Gly Ser Leu His Ser Pro Val Gly Val Cys Ser
305                 310                 315                 320
Ser Thr Gly Asn Ser His Ser Tyr Thr Asn Ser Ser Leu Asn Ala Leu
            325                 330                 335
Gln Ala Leu Ser Glu Gly His Gly Val Ser Leu Gly Ser Ser Leu Ala
            340                 345                 350
Ser Pro Asp Leu Lys Met Gly Asn Leu Gln Asn Ser Pro Val Asn Met
            355                 360                 365
Asn Pro Pro Leu Ser Lys Met Gly Ser Leu Asp Ser Lys Asp Cys
            370                 375                 380
Phe Gly Leu Tyr Gly Glu Pro Ser Glu Gly Thr Thr Gly Gln Ala Glu
385                 390                 395                 400
Ser Ser Cys His Pro Gly Glu Gln Lys Glu Thr Asn Asp Pro Asn Leu
            405                 410                 415
Pro Pro Ala Val Ser Ser Glu Arg Ala Asp Gly Gln Ser Arg Leu His
            420                 425                 430
Asp Ser Lys Gly Gln Thr Lys Leu Leu Gln Leu Leu Thr Thr Lys Ser
            435                 440                 445
Asp Gln Met Glu Pro Ser Pro Leu Ala Ser Ser Leu Ser Asp Thr Asn
450                 455                 460
Lys Asp Ser Thr Gly Ser Leu Pro Gly Ser Gly Ser Thr His Gly Thr
465                 470                 475                 480
Ser Leu Lys Glu Lys His Lys Ile Leu His Arg Leu Leu Gln Asp Ser
            485                 490                 495
Ser Ser Pro Val Asp Leu Ala Lys Leu Thr Ala Glu Ala Thr Gly Lys
            500                 505                 510
Asp Leu Ser Gln Glu Ser Ser Ser Thr Ala Pro Gly Ser Glu Val Thr
            515                 520                 525
Ile Lys Gln Glu Pro Val Ser Pro Lys Lys Lys Glu Asn Ala Leu Leu
            530                 535                 540
Arg Tyr Leu Leu Asp Lys Asp Thr Lys Asp Ile Gly Leu Pro Glu
545                 550                 555                 560
Ile Thr Pro Lys Leu Glu Arg Leu Asp Ser Lys Thr Asp Pro Ala Ser
            565                 570                 575
Asn Thr Lys Leu Ile Ala Met Lys Thr Glu Lys Glu Glu Met Ser Phe
```

-continued

```
                    580                 585                 590
Glu Pro Gly Asp Gln Pro Gly Ser Glu Leu Asp Asn Leu Glu Ile
            595                 600                 605
Leu Asp Asp Leu Gln Asn Ser Gln Leu Pro Gln Leu Phe Pro Asp Thr
610                 615                 620
Arg Pro Gly Ala Pro Ala Gly Ser Val Asp Lys Gln Ala Ile Ile Asn
625                 630                 635                 640
Asp Leu Met Gln Leu Thr Ala Glu Asn Ser Pro Val Thr Pro Val Gly
                    645                 650                 655
Ala Gln Lys Thr Ala Leu Arg Ile Ser Gln Ser Thr Phe Asn Asn Pro
            660                 665                 670
Arg Pro Gly Gln Leu Gly Arg Leu Pro Asn Gln Asn Leu Pro Leu
            675                 680                 685
Asp Ile Thr Leu Gln Ser Pro Thr Gly Ala Gly Pro Phe Pro Pro Ile
        690                 695                 700
Arg Asn Ser Ser Pro Tyr Ser Val Ile Pro Gln Pro Gly Met Met Gly
705                 710                 715                 720
Asn Gln Gly Met Ile Gly Asn Gln Gly Asn Leu Gly Asn Ser Ser Thr
                    725                 730                 735
Gly Met Ile Gly Asn Ser Ala Ser Arg Pro Thr Met Pro Ser Gly Glu
            740                 745                 750
Trp Ala Pro Gln Ser Ser Ala Val Arg Val Thr Cys Ala Ala Thr Thr
            755                 760                 765
Ser Ala Met Asn Arg Pro Val Gln Gly Gly Met Ile Arg Asn Pro Ala
770                 775                 780
Ala Ser Ile Pro Met Arg Pro Ser Ser Gln Pro Gly Gln Arg Gln Thr
785                 790                 795                 800
Leu Gln Ser Gln Val Met Asn Ile Gly Pro Ser Glu Leu Glu Met Asn
                    805                 810                 815
Met Gly Gly Pro Gln Tyr Ser Gln Gln Ala Pro Pro Asn Gln Thr
            820                 825                 830
Ala Pro Trp Pro Glu Ser Ile Leu Pro Ile Asp Gln Ala Ser Phe Ala
            835                 840                 845
Ser Gln Asn Arg Gln Pro Phe Gly Ser Ser Pro Asp Asp Leu Leu Cys
850                 855                 860
Pro His Pro Ala Ala Glu Ser Pro Ser Asp Glu Gly Ala Leu Leu Asp
865                 870                 875                 880
Gln Leu Tyr Leu Ala Leu Arg Asn Phe Asp Gly Leu Glu Glu Ile Asp
                    885                 890                 895
Arg Ala Leu Gly Ile Pro Glu Leu Val Ser Gln Ser Gln Ala Val Asp
                    900                 905                 910
Pro Glu Gln Phe Ser Ser Gln Asp Ser Asn Ile Met Leu Glu Gln Lys
            915                 920                 925
Ala Pro Val Phe Pro Gln Gln Tyr Ala Ser Gln Ala Gln Met Ala Gln
            930                 935                 940
Gly Ser Tyr Ser Pro Met Gln Asp Pro Asn Phe His Thr Met Gly Gln
945                 950                 955                 960
Arg Pro Ser Tyr Ala Thr Leu Arg Met Gln Pro Arg Pro Gly Leu Arg
                    965                 970                 975
Pro Thr Gly Leu Val Gln Asn Gln Pro Asn Gln Leu Arg Leu Gln Leu
            980                 985                 990
Gln His Arg Leu Gln Ala Gln Gln Asn Arg Gln Pro Leu Met Asn Gln
        995                 1000                1005
```

-continued

```
Ile Ser Asn Val Ser Asn Val Asn Leu Thr Leu Arg Pro Gly Val Pro
    1010                1015                1020

Thr Gln Ala Pro Ile Asn Ala Gln Met Leu Ala Gln Arg Gln Arg Glu
1025                1030                1035                1040

Ile Leu Asn Gln His Leu Arg Gln Arg Gln Met His Gln Gln Gln Gln
                1045                1050                1055

Val Gln Gln Arg Thr Leu Met Met Arg Gly Gln Gly Leu Asn Met Thr
            1060                1065                1070

Pro Ser Met Val Ala Pro Ser Gly Met Pro Ala Thr Met Ser Asn Pro
        1075                1080                1085

Arg Ile Pro Gln Ala Asn Ala Gln Gln Phe Pro Phe Pro Pro Asn Tyr
    1090                1095                1100

Gly Ile Ser Gln Gln Pro Asp Pro Gly Phe Thr Gly Ala Thr Thr Pro
1105                1110                1115                1120

Gln Ser Pro Leu Met Ser Pro Arg Met Ala His Thr Gln Ser Pro Met
                1125                1130                1135

Met Gln Gln Ser Gln Ala Asn Pro Ala Tyr Gln Ala Pro Ser Asp Ile
            1140                1145                1150

Asn Gly Trp Ala Gln Gly Asn Met Gly Gly Asn Ser Met Phe Ser Gln
        1155                1160                1165

Gln Ser Pro Pro His Phe Gly Gln Gln Ala Asn Thr Ser Met Tyr Ser
    1170                1175                1180

Asn Asn Met Asn Ile Asn Val Ser Met Ala Thr Asn Thr Gly Gly Met
1185                1190                1195                1200

Ser Ser Met Asn Gln Met Thr Gly Gln Ile Ser Met Thr Ser Val Thr
                1205                1210                1215

Ser Val Pro Thr Ser Gly Leu Ser Ser Met Gly Pro Glu Gln Val Asn
            1220                1225                1230

Asp Pro Ala Leu Arg Gly Gly Asn Leu Phe Pro Asn Gln Leu Pro Gly
        1235                1240                1245

Met Asp Met Ile Lys Gln Glu Gly Asp Thr Thr Arg Lys Tyr Cys
    1250                1255                1260

<210> SEQ ID NO 4
<211> LENGTH: 6158
<212> TYPE: DNA
<213> ORGANISM: Homo sapiens

<400> SEQUENCE: 4
ggcggccgca gcctcggcta cagcttcggc ggcgaaggtc agcgccgacg gcagccggca      60
cctgacggcg tgaccgaccc gagccgattt ctcttggatt tggctacaca cttatagatc     120
ttctgcactg tttacaggca cagttgctga tatgtgttca agatgagtgg gatgggagaa     180
aatacctctg accctccag ggcagagaca agaaagcgca aggaatgtcc tgaccaactt      240
ggacccagcc ccaaaaggaa cactgaaaaa cgtaatcgtg aacaggaaaa taaatatata     300
gaagaacttg cagagttgat ttttgcaaat tttaatgata tagacaactt taacttcaaa     360
cctgacaaat gtgcaatctt aaaagaaact gtgaagcaaa ttcgtcagat caaagaacaa     420
gagaaagcag cagctgccaa catagatgaa gtgcagaagt cagatgtatc ctctacaggg     480
cagggtgtca tcgacaagga tgcgctgggg cctatgatgc ttgaggccct tgatgggttc     540
ttctttgtag tgaacctgga aggcaacgtt gtgtttgtgt cagagaatgt gacacagtat     600
ctaaggtata accaagaaga gctgatgaac aaaagtgtat atagcatctt gcatgttggg     660
```

-continued

```
gaccacacgg aatttgtcaa aaacctgctg ccaaagtcta taggtaaatg ggggatcttg      720
gtctggcgaa cctccgaggc ggaacagcca taccttcaat tgtcggatgc tggtaaaacc      780
tttacctgat tcagaagagg agggtcatga taaccaggaa gctcatcaga aatatgaaac      840
tatgcagtgc ttcgctgtct ctcaaccaaa gtccatcaaa gaagaaggag aagatttgca      900
gtcctgcttg atttgcgtgg caagaagagt tcccatgaag gaaagaccag ttcttccctc      960
atcagaaagt tttactactc gccaggatct ccaaggcaag atcacgtctc tggataccag     1020
caccatgaga gcagccatga aaccaggctg ggaggacctg gtaagaaggt gtattcagaa     1080
gttccatgcg cagcatgaag gagaatctgt gtcctatgct aagaggcatc atcatgaagt     1140
actgagacaa ggattggcat tcagtcaaat ctatcgtttt tccttgtctg atggcactct     1200
tgttgctgca caaacgaaga gcaaactcat ccgttctcag actactaatg aacctcaact     1260
tgtaatatct ttacatatgc ttcacagaga gcagaatgtg tgtgtgatga atccggatct     1320
gactggacaa acgatgggga agccactgaa tccaattagc tctaacagcc ctgcccatca     1380
ggccctgtgc agtgggaacc caggtcagga catgaccctc agtagcaata taaattttcc     1440
cataaatggc ccaaaggaac aaatgggcat gcccatgggc aggtttggtg gttctggggg     1500
aatgaaccat gtgtcaggca tgcaagcaac cactcctcag ggtagtaact atgcactcaa     1560
aatgaacagc ccctcacaaa gcagccctgg catgaatcca ggacagccca cctccatgct     1620
ttcaccaagg catcgcatga gccctggagt ggctggcagc cctcgaatcc cacccagtca     1680
gttttcccct gcaggaagct tgcattcccc tgtgggagtt tgcagcagca caggaaaatag     1740 ccatagttat accaacagct ccctcaatgc acttcaggcc ctcagcgagg ggcacggggt     1800
ctcattaggg tcatcgttgg cttcaccaga cctaaaaatg gcaatttgc aaaactcccc     1860 agttaatatg aatcctcccc cactcagcaa gatgggaagc ttggactcaa aagactgttt     1920
tggactatat ggggagccct ctgaaggtac aactggacaa gcagagagca gctgccatcc     1980
tggagagcaa aaggaaacaa atgaccccaa cctgcccccg gccgtgagca gtgagagagc     2040
tgacgggcag agcagactgc atgacagcaa agggcagacc aaactcctgc agctgctgac     2100
caccaaatct gatcagatgg agccctcgcc cttagccagc tctttgtcgg atacaaacaa     2160
agactccaca ggtagcttgc ctggttctgg gtctacacat ggaacctcgc tcaaggagaa     2220
gcataaaatt ttgcacagac tcttgcagga cagcagttcc cctgtggact tggccaagtt     2280
aacagcagaa gccacaggca aagacctgag ccaggagtcc agcagcacag ctcctggatc     2340
agaagtgact attaaacaag agccggtgag ccccaagaag aaagagaatg cactacttcg     2400
ctatttgcta gataaagatg atactaaaga tattggtttta ccagaaataa cccccaaact     2460
tgagagactg gacagtaaga cagatcctgc cagtaacaca aaattaatag caatgaaaac     2520
tgagaaggag gagatgagct ttgagcctgg tgaccagcct ggcagtgagc tggacaactt     2580
ggaggagatt ttgdatgatt tgcagaatag tcaattacca cagcttttcc cagacacgag     2640
gccaggcgcc cctgctggat cagttgacaa gcaagccatc atcaatgacc tcatgcaact     2700
cacagctgaa aacagccctg tcacacctgt tggagcccag aaaacagcac tgcgaatttc     2760
acagagcact tttaataacc cacgaccagg gcaactgggc aggttattgc caaaccagaa     2820
tttaccactt gacatcacat tgcaaagccc aactggtgct ggacctttcc caccaatcag     2880
aaacagtagt ccctactcag tgatacctca gccaggaatg atgggtaatc aagggatgat     2940
aggaaaccaa ggaaatttag ggaacagtag cacaggaatg attggtaaca gtgcttctcg     3000
gcctactatg ccatctggag aatgggcacc gcagagttcg gctgtgagag tcacctgtgc     3060
```

-continued

```
tgctaccacc agtgccatga accggccagt ccaaggaggt atgattcgga acccagcagc    3120
cagcatcccc atgaggccca gcagccagcc tggccaaaga cagacgcttc agtctcaggt    3180
catgaatata gggccatctg aattagagat gaacatgggg ggacctcagt atagccaaca    3240
acaagctcct ccaaatcaga ctgccccatg gcctgaaagc atcctgccta tagaccaggc    3300
gtcttttgcc agccaaaaca ggcagccatt tggcagttct ccagatgact tgctatgtcc    3360
acatcctgca gctgagtctc cgagtgatga gggagctctc ctggaccagc tgtatctggc    3420
cttgcggaat tttgatggcc tggaggagat tgatagagcc ttaggaatac ccgaactggt    3480
cagccagagc caagcagtag atccagaaca gttctcaagt caggattcca acatcatgct    3540
ggagcagaag gcgcccgttt cccacagca gtatgcatct caggcacaaa tggcccaggg    3600
tagctattct cccatgcaag atccaaactt tcacaccatg ggacagcggc ctagttatgc    3660
cacactccgt atgcagccca gaccgggcct caggcccacg ggcctagtgc agaaccagcc    3720
aaatcaacta agacttcaac ttcagcatcg cctccaagca cagcagaatc gccagccact    3780
tatgaatcaa atcagcaatg tttccaatgt gaacttgact ctgaggcctg gagtaccaac    3840
acaggcacct attaatgcac agatgctggc ccagagacag agggaaatcc tgaaccagca    3900
tcttcgacag agacaaatgc atcagcaaca gcaagttcag caacgaactt tgatgatgag    3960
aggacaaggg ttgaatatga caccaagcat ggtggctcct agtggtatgc cagcaactat    4020
gagcaaccct cggattcccc aggcaaatgc acagcagttt ccatttcctc caaactacgg    4080
aataagtcag caacctgatc caggctttac tggggctacg actccccaga gcccacttat    4140
gtcaccccga atggcacata cacagagtcc catgatgcaa cagtctcagg ccaacccagc    4200
ctatcaggcc ccctccgaca taaatggatg gcgcagggg aacatgggcg gaaacagcat    4260
gttttcccag cagtccccac cacactttgg gcagcaagca acaccagca tgtacagtaa    4320
caacatgaac atcaatgtgt ccatggcgac caacacaggt ggcatgagca gcatgaacca    4380
gatgacagga cagatcagca tgacctcagt gacctcgtg cctacgtcag ggctgtcctc    4440
catgggtccc gagcaggtta atgatcctgc tctgagggga gcaacctgt cccaaaacca    4500
gctgcctgga atggatatga ttaagcagga gggagacaca acacggaaat attgctgaca    4560
ctgctgaagc cagttgcttc ttcagctgac cgggctcact tgctcaaaac acttccagtc    4620
tggagagctg tgtctatttg tttcaaccca actgacctgc cagccggttc tgctagagca    4680
gacaggcctg gccctggttc ccagggtggc gtccactcgg ctgtggcagg aggagctgcc    4740
tcttctcttg acagtctgaa gctcgcatcc agacagtcgc tcagtctgtt cactgcattc    4800
acctagtgc aacttagatc tctcctgcaa aagtaaatgt tgacaggcaa atttcatacc    4860
catgtcagat tgaatgtatt taaatgtatg tatttaagga gaaccatgct cttgttctgt    4920
tcctgttcgg ttccagacac tggtttcttg ctttgttttc cctggctaac agtctagtgc    4980
aaaagattaa gattttatct gggggaaaga aaagaatttt ttaaaaaatt aaactaaaga    5040
tgttttaagc taaagcctga atttgggatg gaagcaggac agacaccgtg gacagcgctg    5100
tatttacaga cacacccagt gcgtgaagac caacaaagtc acagtcgtat ctctagaaag    5160
ctctaaagac catgttggaa agagtctcca gttactgaac agatgaaaag gagcctgtga    5220
gagggctgtt aacattagca aatattttt ccttgttttt tctttgttaa aaccaaactg    5280
gttcacctga atcatgaatt gagaagaaat aattttcatt tctaaattaa gtcccttta    5340
gtttgatcag acagcttgaa tcagcatctc ttcttccctg tcagcctgac tcttccttc    5400
```

| | | | | |
|---|---|---|---|---|
| ccctctctca | ttccccatac | tccctatttt | cattccttt | ttaaaaaata atataagcta | 5460 |
| cagaaaccag | gtaagccctt | tatttcctta | aatgttttgc | cagccactta ccaattgcta | 5520 |
| agtattgaat | ttcagaaaaa | aaaaatgcat | ttactggcaa | ggagaagagc aaagttaagg | 5580 |
| cttgatacca | atcgagctaa | ggatacctgc | tttggaagca | tgtttattct gttccccagc | 5640 |
| aactctggcc | tccaaaatgg | gagaaaacgc | cagtgtgttt | aaattgatag cagatatcac | 5700 |
| gacagattta | acctctgcca | tgtgttttt | attttgtttt | ttagcagtgc tgactaagcc | 5760 |
| gaagttttgt | aaggtacata | aaatccaatt | tatatgtaaa | caagcaataa tttaagttga | 5820 |
| gaacttatgt | gttttaattg | tataatttt | gtgaggtata | catattgtgg aattgactca | 5880 |
| aaaatgaggt | acttcagtat | taaattagat | atcttcatag | caatgtctcc taaaggtgtt | 5940 |
| ttgtaaagga | tatcaatgcc | ttgattagac | ctaatttgta | gacttaagac tttttatttt | 6000 |
| ctaaaccttg | tgattctgct | tataagtcat | ttatctaatc | tatatgatat gcagccgctg | 6060 |
| taggaaccaa | ttcttgattt | ttatatgttt | atattctttc | ttaatgaacc ttagaaagac | 6120 |
| tacatgttac | taagcaggcc | acttttatgg | ttgttttt | | 6158 |

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccagggtga ataacctcgg ggctctgtcc ctccaatccc agggtgaata acctcggg        58